(12) United States Patent
Solotoff

(10) Patent No.: US 11,839,564 B1
(45) Date of Patent: Dec. 12, 2023

(54) KNEE ORTHOSIS, ADJUSTABLE

(71) Applicant: PREFERRED PRESCRIPTION INC., Hollywood, FL (US)

(72) Inventor: Brandon Solotoff, Boca Raton, FL (US)

(73) Assignee: Preferred Prescription, INC, Hollywood, FL (US)

(*) Notice: Subject to any disclaimer, the term of this patent is extended or adjusted under 35 U.S.C. 154(b) by 634 days.

(21) Appl. No.: 16/986,345

(22) Filed: Aug. 6, 2020

Related U.S. Application Data

(60) Provisional application No. 62/925,291, filed on Oct. 24, 2019, provisional application No. 62/925,289, filed on Oct. 24, 2019, provisional application No. 62/899,258, filed on Sep. 12, 2019, provisional application No. 62/884,262, filed on Aug. 8, 2019.

(51) Int. Cl.
*A61F 5/01* (2006.01)

(52) U.S. Cl.
CPC .... *A61F 5/0125* (2013.01); *A61F 2005/0155* (2013.01); *A61F 2005/0172* (2013.01)

(58) Field of Classification Search
CPC ............ A61F 5/0125; A61F 2005/0155; A61F 2005/0172; A61F 5/0123; A61F 5/0106; A61F 5/01; A61F 5/0134; A61F 5/0137; A61F 5/0139; A61F 5/0141; A61F 5/0148; A61F 2007/0041; A61F 13/061;
(Continued)

(56) References Cited

U.S. PATENT DOCUMENTS 2,308,776 A 1/1943 Peckham
3,046,981 A 7/1962 Biggs
(Continued)

FOREIGN PATENT DOCUMENTS

CN 203915158 U 11/2014
CN 105443565 B 3/2016
(Continued)

OTHER PUBLICATIONS

Press Fit Forces Stress Design Calculator, Jun. 18, 2018, available at: www.engineersedge.com/calculators/machine-design/press-fit/press-fit.htm.
(Continued)

*Primary Examiner* — Tarla R Patel
(74) *Attorney, Agent, or Firm* — Thomas A. O'Rourke; James Bongiorno

(57) ABSTRACT

A knee brace includes a first portion for securement to the thigh region, a second portion for securement to the calf region, and pivotal coupling of the upper region to the lower region. A special pad is used for contacting each region of the leg, which pad is received in a shell that includes a plurality of ventilation openings, and which pad includes a plurality of thru-openings interconnected with the ventilation openings in the shell, and grooves that interconnect the plurality of openings in the pad. The openings and grooves in the pad serve to better grip the wearer's leg and reduce the tensioning needed by the straps to maintain the brace in position. The upper cuff and/or lower cuff may be adjustably secured to the arms of the hinge using T-shaped mounting studs that mate with a corresponding cruciform-shaped opening in the hinge arms.

14 Claims, 36 Drawing Sheets

(58) Field of Classification Search
CPC .. A61F 2/38; A61F 2/3886; A61F 2/64; A61F 2007/0042

See application file for complete search history.

(56) References Cited

U.S. PATENT DOCUMENTS

| | | | |
|---|---|---|---|
| 3,662,435 A | | 5/1972 | Allsop |
| 3,749,366 A | | 7/1973 | Brucker |
| 4,088,130 A | | 5/1978 | Applegate |
| 4,090,508 A | | 5/1978 | Gaylord |
| 4,185,360 A | | 1/1980 | Prete |
| 4,240,414 A | | 12/1980 | Theisler |
| 4,256,097 A | | 3/1981 | Willis |
| 4,428,369 A | | 1/1984 | Peckham |
| 4,493,316 A | | 1/1985 | Reed |
| 4,572,170 A | | 2/1986 | Cronk |
| 4,576,151 A | | 3/1986 | Carmichael |
| 4,632,098 A | | 12/1986 | Grundei |
| 4,732,143 A | | 3/1988 | Kausek |
| 4,768,500 A | | 9/1988 | Mason |
| 4,803,975 A | | 2/1989 | Meyers |
| 4,805,606 A | | 2/1989 | McDavid |
| 4,817,588 A | | 4/1989 | Bledsoe |
| 4,940,044 A | | 7/1990 | Castillo |
| 4,982,732 A | | 1/1991 | Morris |
| 4,986,264 A | | 1/1991 | Miller |
| 5,000,169 A | | 3/1991 | Swicegood |
| 5,038,763 A | | 8/1991 | Wiggins |
| 5,039,247 A | | 8/1991 | Young |
| 5,060,640 A | | 10/1991 | Rasmusson |
| 5,062,858 A | | 11/1991 | Broeck |
| 5,086,760 A | | 2/1992 | Neumann |
| 5,277,698 A | | 1/1994 | Taylor |
| 5,302,169 A | | 4/1994 | Taylor |
| 5,358,469 A | | 10/1994 | Patchel |
| 5,403,002 A | | 4/1995 | Brunty |
| 5,409,449 A | | 4/1995 | Nebolon |
| 5,419,754 A | | 5/1995 | Hutchins |
| 5,421,810 A | * | 6/1995 | Davis .................... A61F 5/0193 602/26 |
| 5,443,444 A | | 8/1995 | Pruyssers |
| 5,458,565 A | | 10/1995 | Tillinghast |
| 5,460,599 A | | 10/1995 | Davis |
| 5,472,410 A | | 12/1995 | Hamersly |
| 5,558,627 A | | 9/1996 | Singer |
| 5,658,243 A | | 8/1997 | Miller |
| 5,672,152 A | | 9/1997 | Mason |
| 5,814,000 A | | 9/1998 | Kilby |
| 5,817,040 A | | 10/1998 | Hess |
| 6,203,511 B1 | | 3/2001 | Johnson |
| 6,527,733 B1 | | 3/2003 | Ceriani |
| 6,547,218 B2 | | 4/2003 | Landy |
| 6,993,808 B1 | | 2/2006 | Bennett |
| 7,189,212 B2 | | 3/2007 | Popp |
| 7,198,610 B2 | | 4/2007 | Infimundarson |
| 7,201,728 B2 | | 4/2007 | Sterling |
| 7,235,059 B2 | | 6/2007 | Mason |
| 7,285,103 B2 | | 10/2007 | Nathanson |
| 7,473,234 B1 | | 1/2009 | Weltner |
| 7,597,675 B2 | | 10/2009 | Ingimundarson |
| 7,713,225 B2 | | 5/2010 | Ingimundarson |
| 7,794,418 B2 | | 9/2010 | Ingimundarson |
| 7,819,830 B2 | | 10/2010 | Sindel |
| 8,277,401 B2 | | 10/2012 | Hammerslag |
| 9,125,730 B2 | | 9/2015 | Ingimundarson |
| 9,351,864 B2 | | 5/2016 | Romo |
| 2007/0213648 A1 | | 9/2007 | Ferrigolo |
| 2014/0005583 A1 | * | 1/2014 | Cardinali .............. A61F 5/0123 602/5 |
| 2014/0124557 A1 | | 5/2014 | Velare |
| 2019/0159922 A1 | * | 5/2019 | Frost .................... A61F 5/0123 |
| 2019/0240056 A1 | * | 8/2019 | Thor .................... A61F 5/0123 |
| 2023/0000654 A1 | * | 1/2023 | Nordt, III ............. A61F 5/0123 |
| 2023/0147111 A1 | * | 5/2023 | Brookover ............ A61F 5/0123 602/26 |

FOREIGN PATENT DOCUMENTS

| | | |
|---|---|---|
| DE | 19904554 B4 | 8/2000 |
| DE | 60035431 T2 | 3/2008 |
| DE | 102012002554 A1 | 8/2013 |
| EP | 2260799 A1 | 12/2010 |
| EP | 3378448 A2 | 9/2018 |
| GB | 2136294 A | 9/1984 |
| GB | 2163352 A | 2/1986 |
| KR | 20180082516 A | 7/2018 |

OTHER PUBLICATIONS

"Three General Types of Fit," available at www.mmto.org/dclark/Reports/Encoder%20Upgrade/fittolerences%20%5BRead-Only%5D.pdf., Jul. 8, 2019.

"Engineering Fit," available at: https://en.wikipedia.org/wiki/Engineering_fit, Jul. 8, 2019.

* cited by examiner

FIG. 10
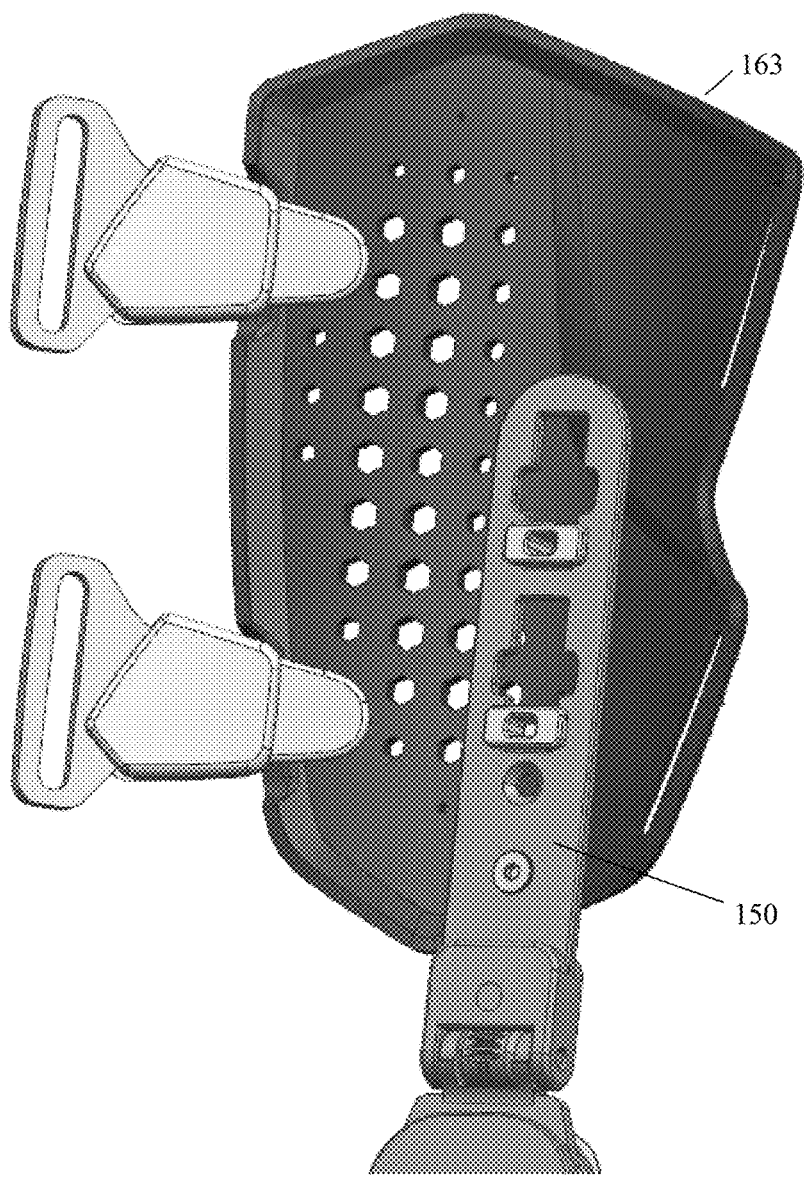
FIG. 10C  FIG. 10B
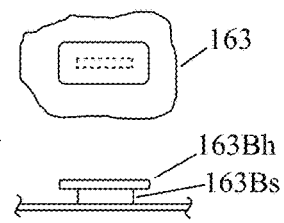
FIG. 10A

400

FIG. 50
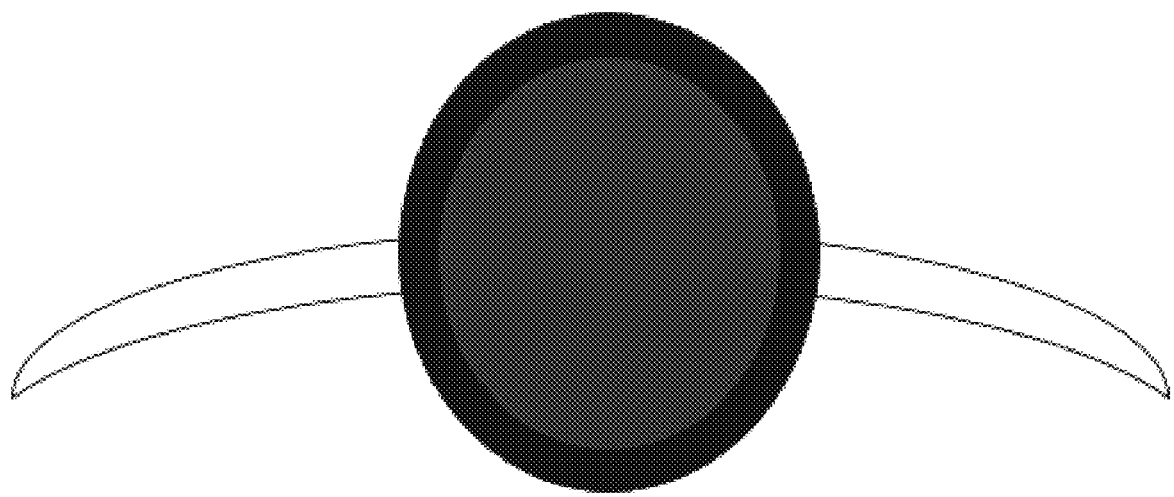
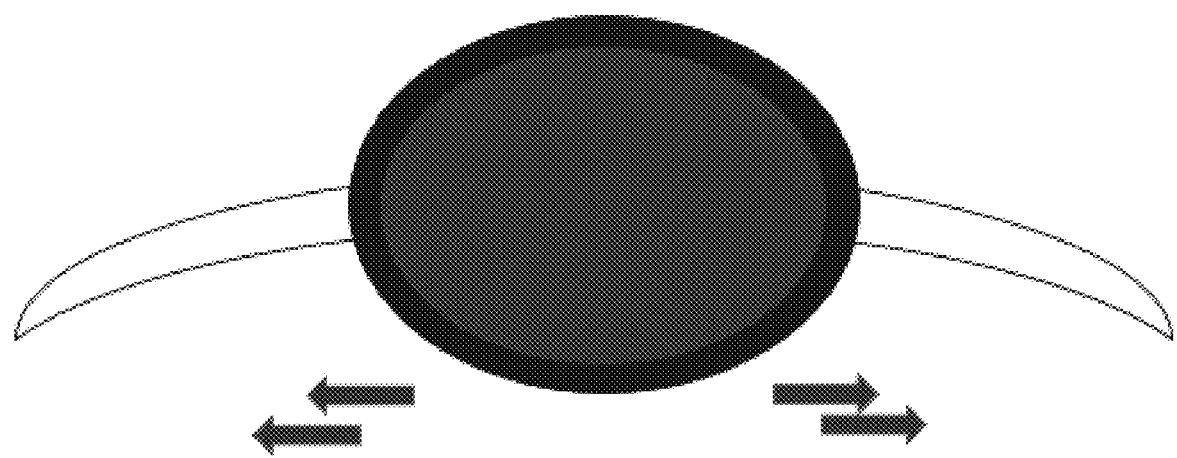
FIG. 51

FIG. 53
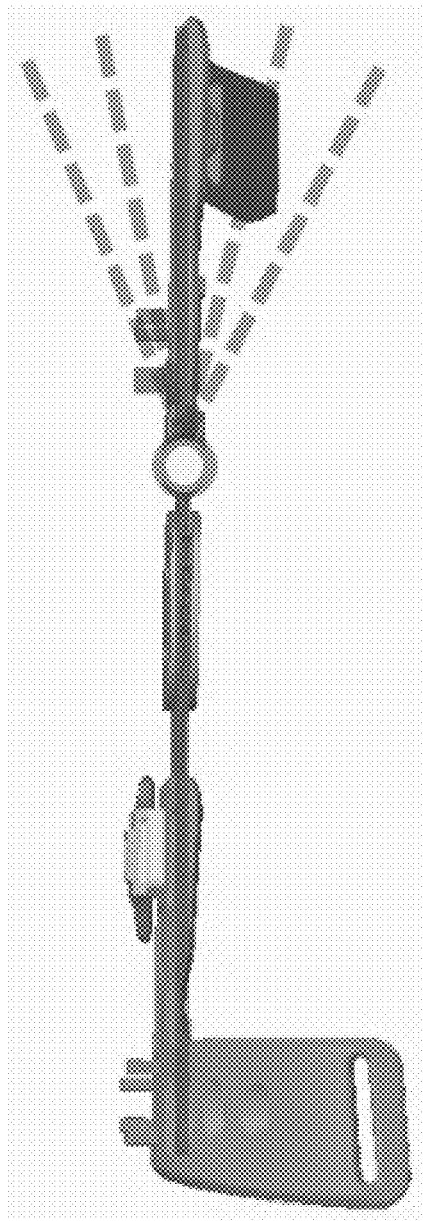
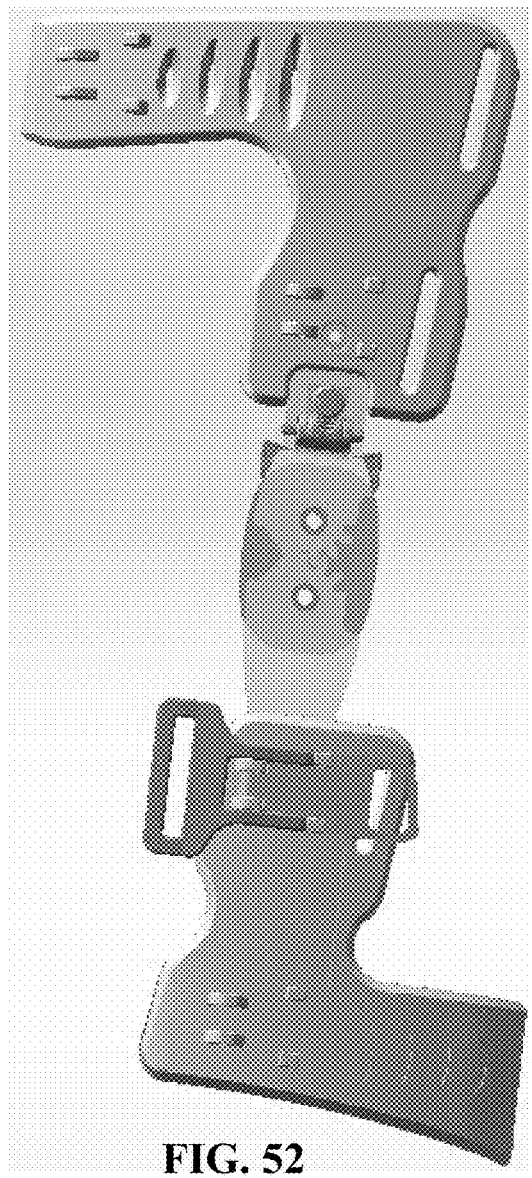
FIG. 52

KNEE ORTHOSIS, ADJUSTABLE

CROSS REFERENCES TO RELATED APPLICATIONS

This application claims priority on the following provisional applications, all disclosures of which are incorporated herein by reference: U.S. Provisional Application Ser. No. 62/884,262, filed on Aug. 8, 2019; U.S. Provisional Application Ser. No. 62/899,258, filed on Sep. 12, 2019; U.S. Provisional Application Ser. No. 62/925,289, filed on Oct. 24, 2019; and U.S. Provisional Application Ser. No. 62/925,291, filed on Oct. 24, 2019.

FIELD OF THE INVENTION

This disclosure relates generally to an orthopedic device, and more particularly to an improved knee orthosis that is adjustable and configured for dynamically supporting the knee during movements of the wearer.

BACKGROUND OF THE INVENTION

Orthopedic doctors generally acknowledge that the most commonly injured joint in the human body is the knee. There are many different types of knee injuries, including, but not limited to, fractures, anterior cruciate ligament injuries (e.g., a torn ACL), dislocation, meniscal tears, bursitis, tendonitis, tendon tears, collateral ligament injuries, Iliotibial band syndrome, posterior cruciate ligament injuries, etc. A knee brace may typically worn to not only prevent the occurrence or reoccurrence of an old knee injury, but also to support the knee joint throughout the range of motion while rehabbing the joint due to one of the above mentioned injuries, or after the recovery process is essentially completed but while the knee may still be somewhat weakened. A knee brace may also be worn to prevent swelling.

Apparatus that may be related, and which are not admitted herein to be prior art to the herein disclosed apparatus, may be shown by the following U.S. Patents and Patent Application Publications: U.S. Pat. No. 3,046,981 to Biggs; U.S. Pat. No. 4,088,130 to Applegate; U.S. Pat. No. 4,090,508 to Gaylord; U.S. Pat. No. 4,240,414 to Theisler; U.S. Pat. No. 4,256,097 to Willis; U.S. Pat. No. 4,493,316 to Reed; U.S. Pat. No. 4,572,170 to Cronk; U.S. Pat. No. 4,576,151 to Carmichael; U.S. Pat. No. 4,632,098 to Grundei; U.S. Pat. No. 4,732,143 to Kausek; U.S. Pat. No. 4,768,500 to Mason; U.S. Pat. No. 4,803,975 to Meyers; U.S. Pat. No. 4,805,606 to McDavid; U.S. Pat. No. 4,817,588 to Bledsoe; U.S. Pat. No. 4,940,044 to Castillo; U.S. Pat. No. 4,986,264 to Miller; U.S. Pat. No. 5,038,763 to Wiggins; U.S. Pat. No. 5,039,247 to Young; U.S. Pat. No. 5,060,640 to Rasmusson; U.S. Pat. No. 5,062,858 to Broeck; U.S. Pat. No. 5,086,760 to Neumann; U.S. Pat. No. 5,277,698 to Taylor; U.S. Pat. No. 5,358,469 to Patchel; U.S. Pat. No. 5,403,002 to Brunty; U.S. Pat. No. 5,419,754 to Hutchins; U.S. Pat. No. 5,421,810 to Davis; U.S. Pat. No. 5,443,444 to Pruyssers; U.S. Pat. No. 5,458,565 to Tillinghast; U.S. Pat. No. 5,472,410 to Hammersly; U.S. Pat. No. 5,558,627 to Singer; U.S. Pat. No. 5,658,243 to Miller; U.S. Pat. No. 5,814,000 to Kilbey; U.S. Pat. No. 5,817,040 to Hess; U.S. Pat. No. 6,527,733 to Ceriani; U.S. Pat. No. 7,189,212 to Popp; U.S. Pat. No. 7,201,728 to Sterling; U.S. Pat. No. 7,306,572 to Ceriani; U.S. Pat. No. 7,473,234 to Weltner; U.S. Pat. No. 7,597,675 to Ingimundarson; U.S. Pat. No. 8,016,781 to Ingimundarson; U.S. Pat. No. 8,062,242 to Ceriani; U.S. Pat. No. 9,377,079 to DeHarde; U.S. Pat. No. 9,668,903 to Hsu; U.S. Pat. No. 9,968,817 to Fields; 2003/0153853 (Houser); 2004/0049140 (Doty); 2004/0068215 (Adelson); 2004/0153015 (Seligman); 2007/0213648 (Ferrigolo); 2007/021947 (Bonutti); 2008/0188356 (Bonutti); and 2015/0057587 (Walsh).

The herein disclosed apparatus provides improvements upon prior art knee braces.

OBJECTS OF THE INVENTION

It is an object of the invention to provide a knee brace having an upper leg cuff securable to the thigh of the wearer; a lower leg cuff securable to the calf of the wearer; an upper support arm fixedly secured to the upper leg cuff; a lower support arm fixedly secured to the lower leg cuff; where the upper support arm is coupled to the lower support arm via a worm drive arrangement and a bicentric hinge assembly.

It is another object of the invention to provide a knee brace having an improved upper cuff and lower cuff arrangement that is comfortably securable to the wearer's thigh, and which also prevents the tight securement thereto from locally restricting blood flow in the person's limbs.

It is a further object of the invention to provide a knee brace having a ratcheting mechanism for the providing tension to the straps of the upper and lower cuffs that permits incremental tensioning of the straps.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with at least one embodiment of the disclosed apparatus, a knee brace may broadly include an upper cuff, and a lower cuff that is pivotally coupled to the upper cuff. Each cuff may be formed of a shell and a pad. The shell includes a plurality of ventilation openings. The pad is secured to the shell and includes a plurality of thru-openings and a plurality of grooves, where each of the plurality of openings in the pad are interconnected by the plurality of grooves. At least a portion of the plurality of openings in the pad are positioned to interconnect with a respective one of the plurality of ventilation openings in the shell, for better heat transfer away from the wearer's leg, for the brace to be cooler while worn. The openings and grooves on the pad may be distributed over at least 80 percent of a surface area of the pad, and serve to better grip the wearer's leg and reduce the tensioning needed by the straps to maintain the brace in position, solving a problem of the prior art braces that tend to cut off the blood flow locally through blood vessel beneath the pad(s) while it was being worn. The shell and the pad for the upper and lower cuffs may be molded into a curved shape to match the corresponding curvature of the wearer's leg.

Another improvement to prior art knee braces includes adjustability of the distance between the upper and lower cuffs. Either or both of the upper cuff and lower cuff may have one mounting stud protruding from the respective shell, where the mounting stud is formed of: a first leg that protrudes away from the shell, and a second leg centrally positioned with respect to a distal end of the first leg to form a T-shape for the mounting stud. The arm of the hinge that corresponds to the shell (i.e., upper arm to upper shell, and lower arm to lower shell) has one cruciform-shaped opening that includes a central open portion that is configured to slidably receive the second leg of the T-shaped mounting stud therethrough in a first direction, and an upper open portion and lower open portion that are each configured to slidably receive the first leg of the T-shaped mounting stud therethrough in respective second and third directions to alternatively couple the arm to the shell at a first adjustment position or a second adjustment position. Two studs and two cruciform-shaped openings may be used for each shell for greater stability. A threaded insert may be positioned in the shell, and which may align with a first hole in the arm when the T-shaped mounting stud is in the first adjustment position, and may align with the second hole in the arm when the T-shaped mounting stud is in the second adjustment position, which arm may be secured at either position using a fastener that may be threadably received in the threaded insert.

Another improvement to prior art knee braces may be a worm drive arrangement in which a dial is secured to the worm gear and configured to manually rotated to rotate the worm gear, to pivot the upper cuff about a lateral axis to a desired angle with respect to the lower cuff, which lateral axis is perpendicular to the hinge axis corresponding to the knee joint movements.

Another improvement to prior art knee braces may be a strap arrangement for securing the cuff(s) to the leg which uses either a levered buckle arrangement or a ratcheting buckle arrangement.

BRIEF DESCRIPTION OF THE DRAWINGS

The description of the various example embodiments is explained in conjunction with appended drawings, in which:

FIG. 10 is a perspective view of the shell for the thigh pad with the upper extension member releasably coupled thereto at a first position;

FIG. 10A is a cross-sectional view through the shell, the stud, and the arm of FIG. 10;

FIG. 10B is a top view of the stud, the arm, and the shell shown in FIG. 10A;

FIG. 10C is a side view of the stud, the arm, and the shell shown in FIG. 10A;

FIG. 50 shows a first embodiment of a slidable support pad that may be positioned on a strap of a knee brace as disclosed herein;

FIG. 51 shows a second embodiment of a slidable support pad that may be positioned on a strap of a knee brace as disclosed herein; and FIGS. 52-53 illustrate rotational positioning of the upper hinge plate of the polycentric hinge to be at different angles with respect to the upper extension arm.

DETAILED DESCRIPTION OF THE INVENTION

Figure 1:
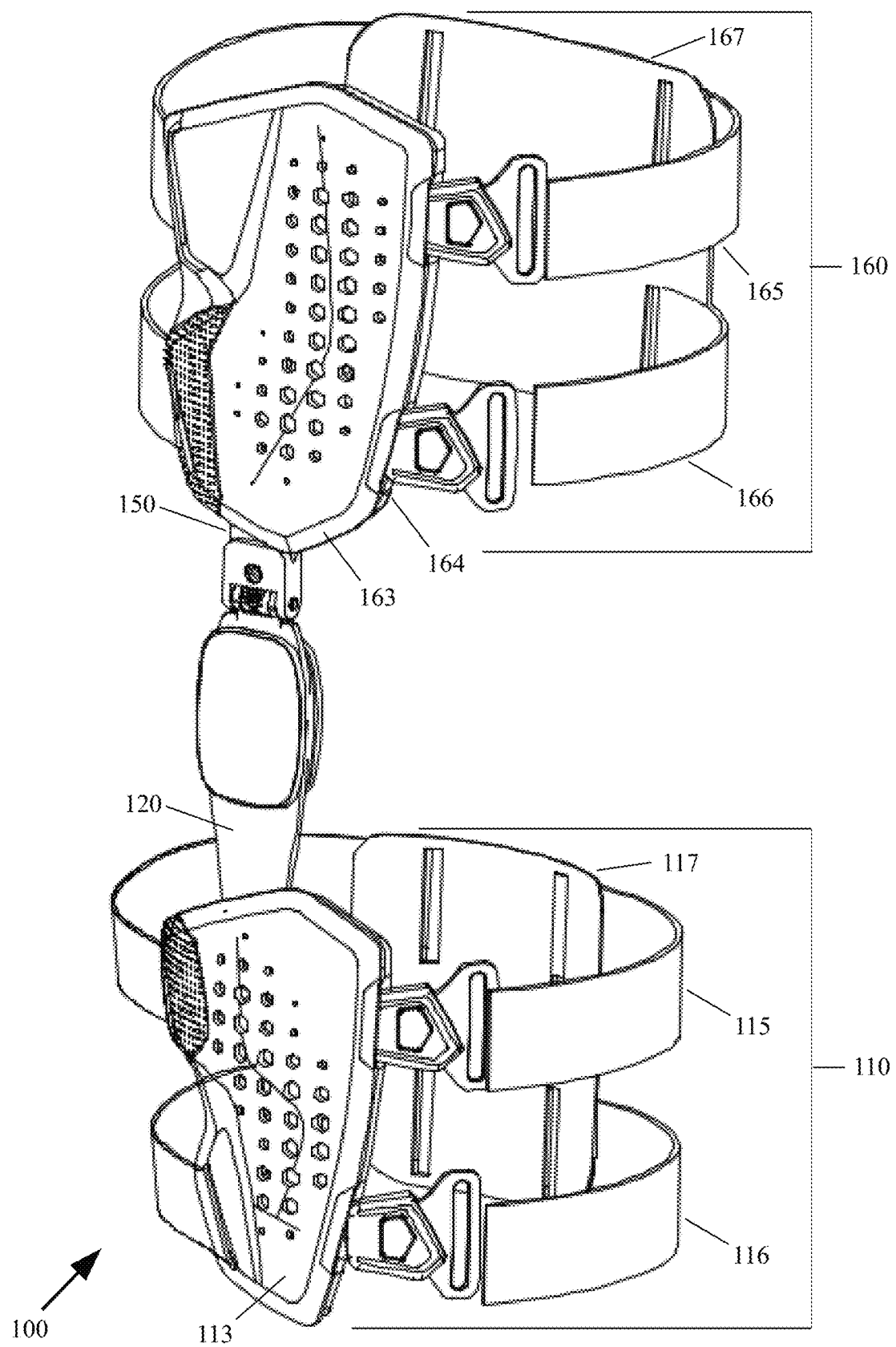
FIG. 1 is a first perspective view of a first embodiment of a knee brace as disclosed herein.
Figure 2:
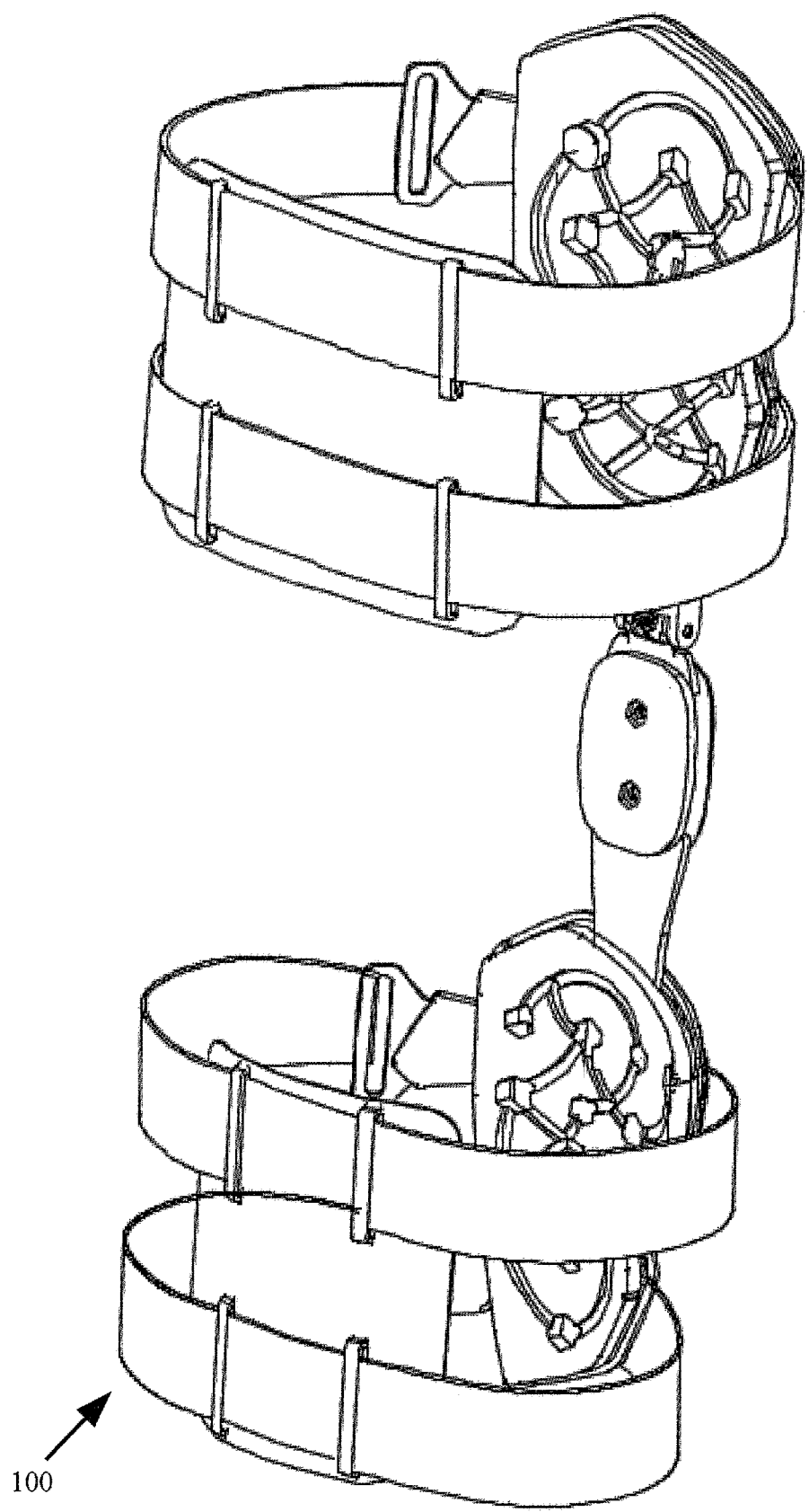
FIG. 2 is a second perspective view of the knee brace of FIG. 1.
Figure 3:
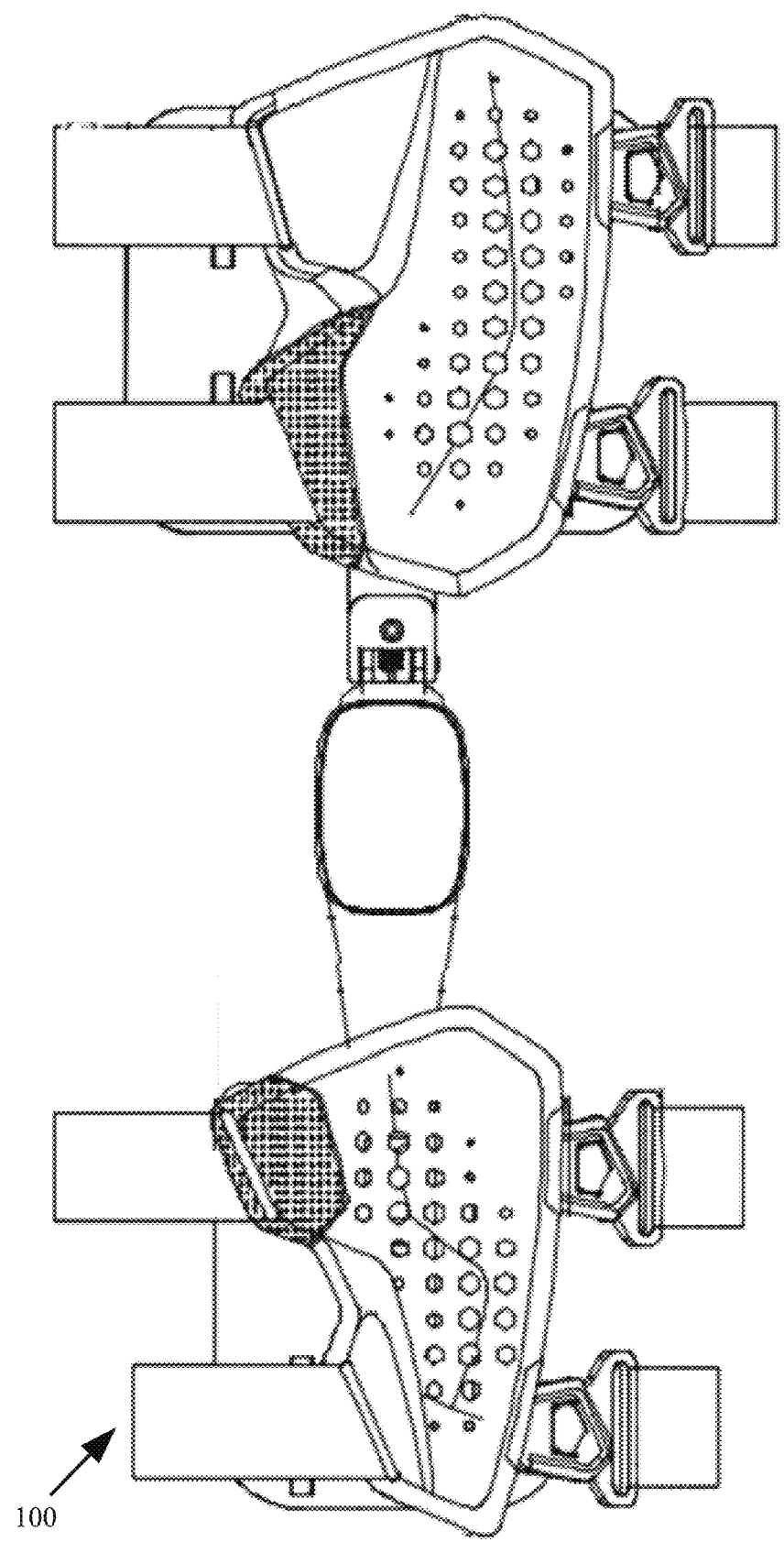
FIG. 3 is a front view of the knee brace of FIG. 1.
Figure 4:
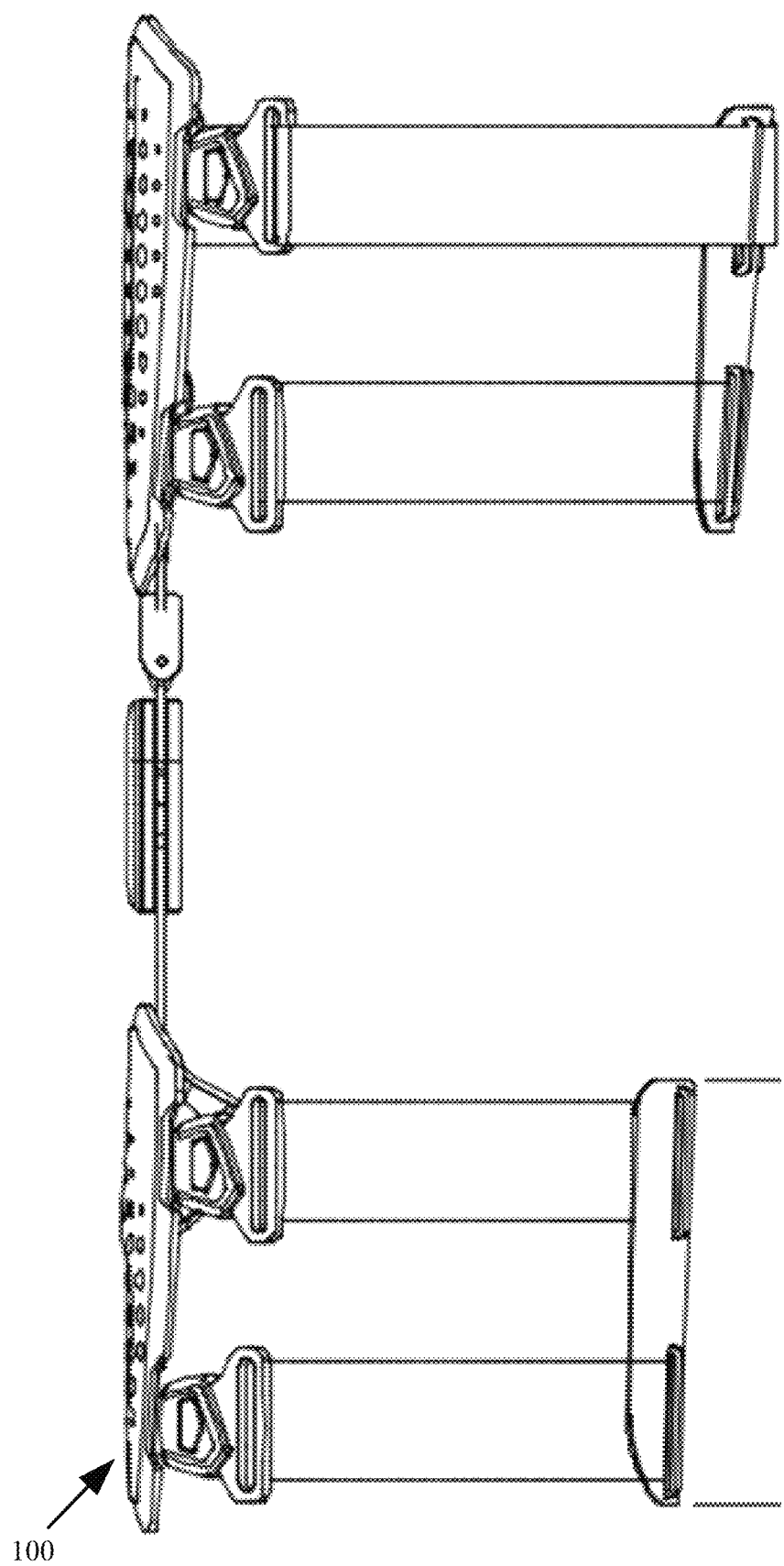
FIG. 4 is a side view of the knee brace of FIG. 1.

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed apparatus.

Furthermore, the described features, advantages, and characteristics of any particular embodiment disclosed herein, may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/calculators/machine-design/press-fit/press-fit-calculator.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit. and may be 0.1360 inches for a free running fit; for a 0.5000 inch diameter shaft the opening may be 0.5156 inches for a close running fit and may be 0.5312 inches for a free running fit). Other clearance amounts are used for other clearance types. See "Engineering Fit" at: https://en.wikipedia.org/wiki/Engineering_fit; and "Three General Types of Fit," available at www.mm-to.org/dclark/Reports/Encoder%20Upgrade/fittolerences%20%5BRead-Only %5D.pdf.

Figure 5:
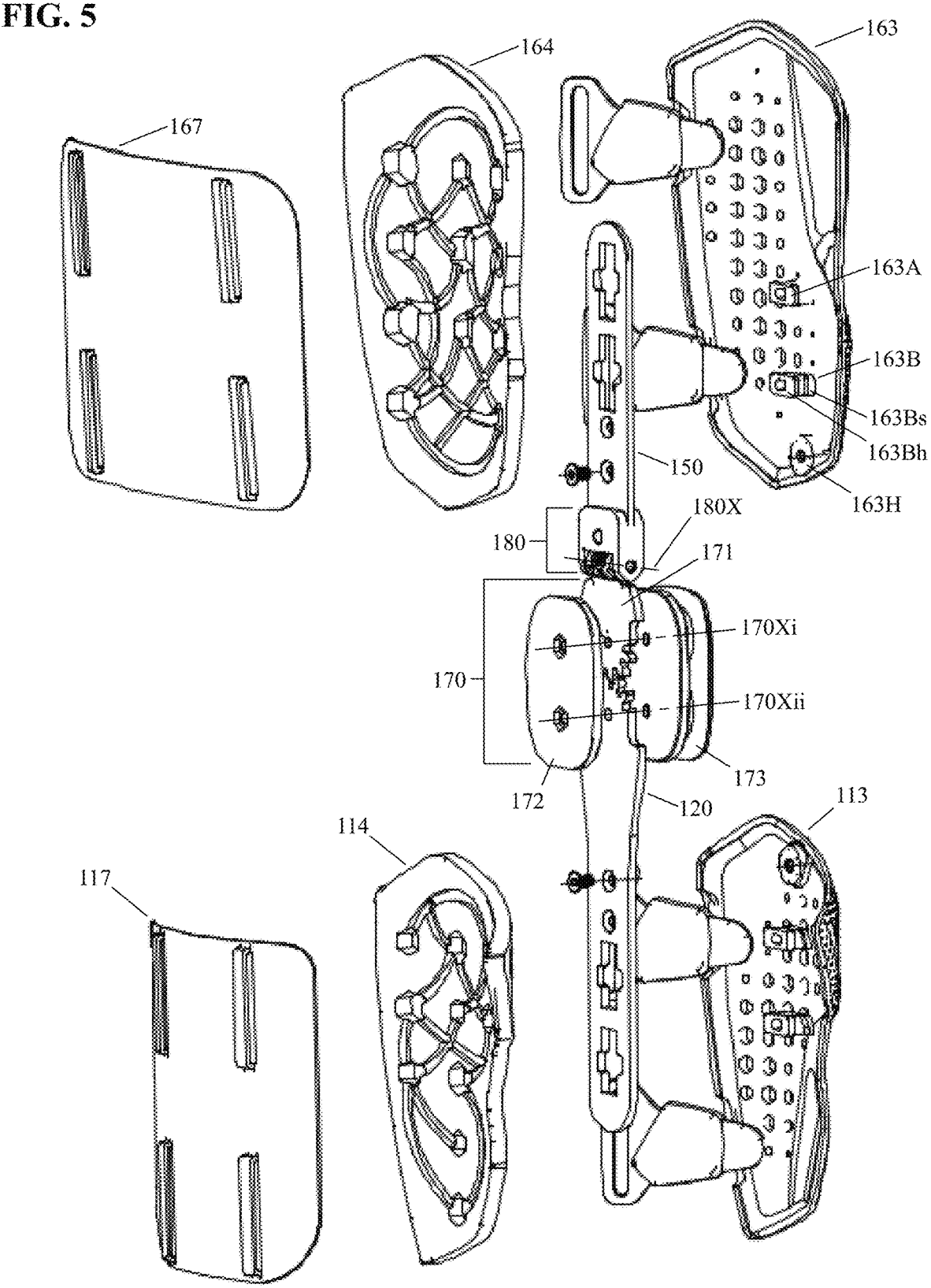
FIG. 5 is an exploded view of the larger component parts of the knee brace of FIG. 1.

As seen in FIGS. 1-4 and the exploded view of FIG. 5, in a first embodiment a knee brace 100 may broadly include a lower cuff assembly 110, an upper cuff assembly 160, and respective lower and upper support arms 120 and 150, which arms may be coupled together via a bicentric hinge and a worm drive arrangement. The bicentric hinge may permit rotational movements of the lower cuff assembly 110 with respect to the upper cuff assembly 150 about first and second rotational axes during movements of the wearer's leg, while the worm drive arrangement may permit a rotational adjustment to the relative angle between the upper and lower cuffs about a third axis being substantially perpendicular to the first and second axes.

The lower cuff assembly 110 may include a lower shell 113, a lower pad 114, and at least one strap 115. In another embodiment the lower cuff assembly 110 may also include a second strap (e.g., straps 115 and 116). In yet another embodiment the lower cuff assembly 110 may include the two straps 115 and 116 which may couple to and support a contact plate 117 that may be padded. The upper cuff assembly 160 may be similarly formed into various different embodiments, which embodiments may include some portion of, or all of: an upper shell 163, an upper pad 164, a strap 165, a strap 166, and a contact plate 167.

Figure 7:
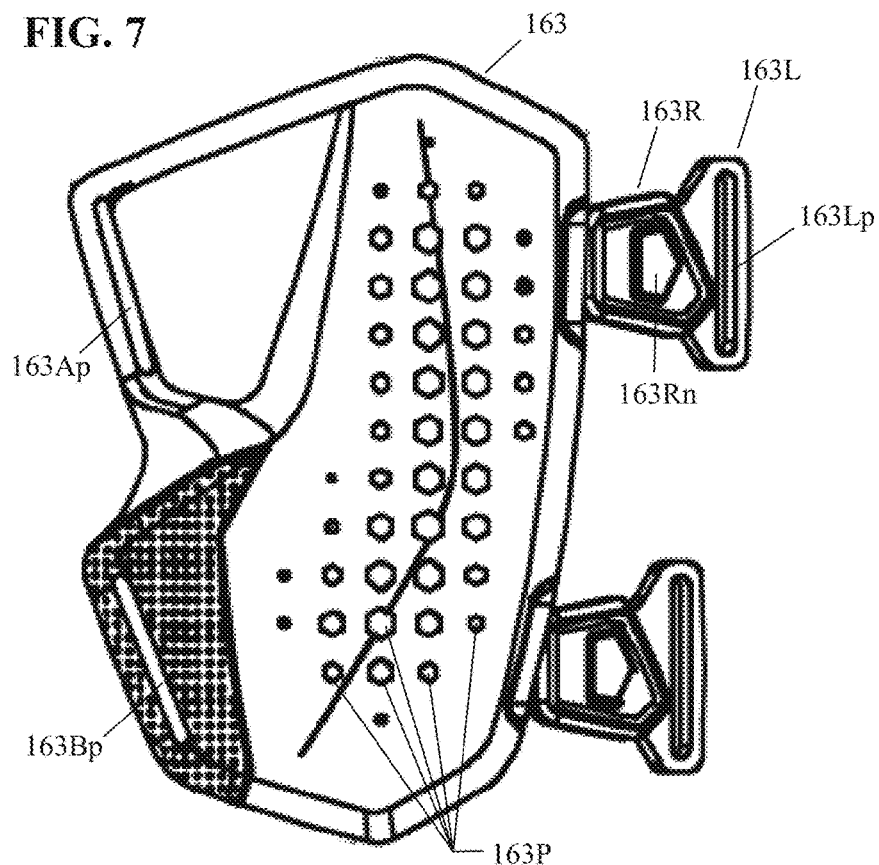
FIG. 7 is a side view of the outward facing side of the shell used to support the thigh pad of the knee brace of FIG. 1.
Figure 8:
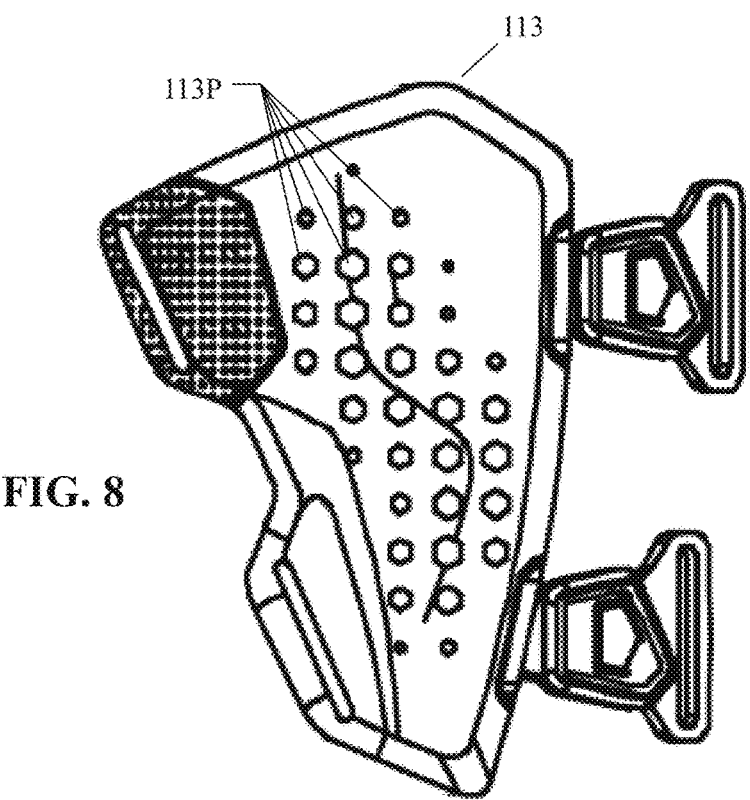
FIG. 8 is a side view of the outward facing side of the shell used to support the calf pad of the knee brace of FIG. 1.

The upper shell 163 and lower shell 113 are shown in FIGS. 7 and 8, respectively. One end of the corresponding straps may be secured to a side of the respective shell in any suitable manner, including, but not limited to, being mechanically fastened thereto such as by using rivets or screws, or by being stitched thereto, etc. In another embodiment each of the upper shell 163 and lower shell 113 may be formed with one or two slotted openings (e.g., slotted openings 163Ap and 163Bp in shell 163 as shown in FIG. 7) to respectively receive a first end of the strap or straps therethrough, which strap(s) may be stitched to itself to form a small loop about the flange formed by the opening(s). The second end of each strap used may be secured to an opposite side of the shell after being looped around the leg of the wearer using any securement arrangement known in the art, including prior art buckle systems, such as those buckles shown by the following U.S. Pat. No. 5,363,863 to Lelli; U.S. Pat. No. 5,911,697 to Biedermann; U.S. Pat. No. 5,500,959 to Yewer; U.S. Pat. No. 5,816,251 to Glisan; U.S. Pat. No. 6,066,108 to Lundberg; U.S. Pat. No. 5,388,274 to Glover; U.S. Pat. No. 4,428,369 to Peckham; U.S. Pat. No. 6,402,713 to Doyle; and U.S. Pat. No. 4,240,414 to Theisler. In another embodiment a blade and receptacle buckle arrangement may be used that may be the same as is found on a standard automobile seat belt arrangement, where, as seen in FIG. 7, the strap is looped about and secured to the opening 163Lp in the blade 163L, and the blade may be releasably coupled to the receptacle 163R and be released therefrom by depressing the button 163Rn.

Both the upper shell 113 and the lower shell 163 may each be formed with a respective plurality of openings 113P and 163P, at least some of which may interconnect to openings in the respective pads 114/164.

As seen in FIGS. 10-11 and FIGS. 16-17, prior to mating of the pads with the shells, which mating shell and pad may have correspondingly shaped peripheries, the upper extension arm 150 may be joined to the upper shell 163 in any suitable manner known in the art, and the lower extension arm 120 may similarly be joined to the lower shell 113. In one embodiment, as may be understood from FIG. 10, the upper extension arm 150 and upper shell 163 may be adjustably joined using one particularly shaped opening in the extension arm that may be slidably coupled to a particularly shaped stud formed on or attached to the shell. In another embodiment, to provide greater connectivity, two particularly shaped openings in the extension arm may be slidably coupled to a corresponding pair of particularly shaped studs formed on the shell.

Figure 9:
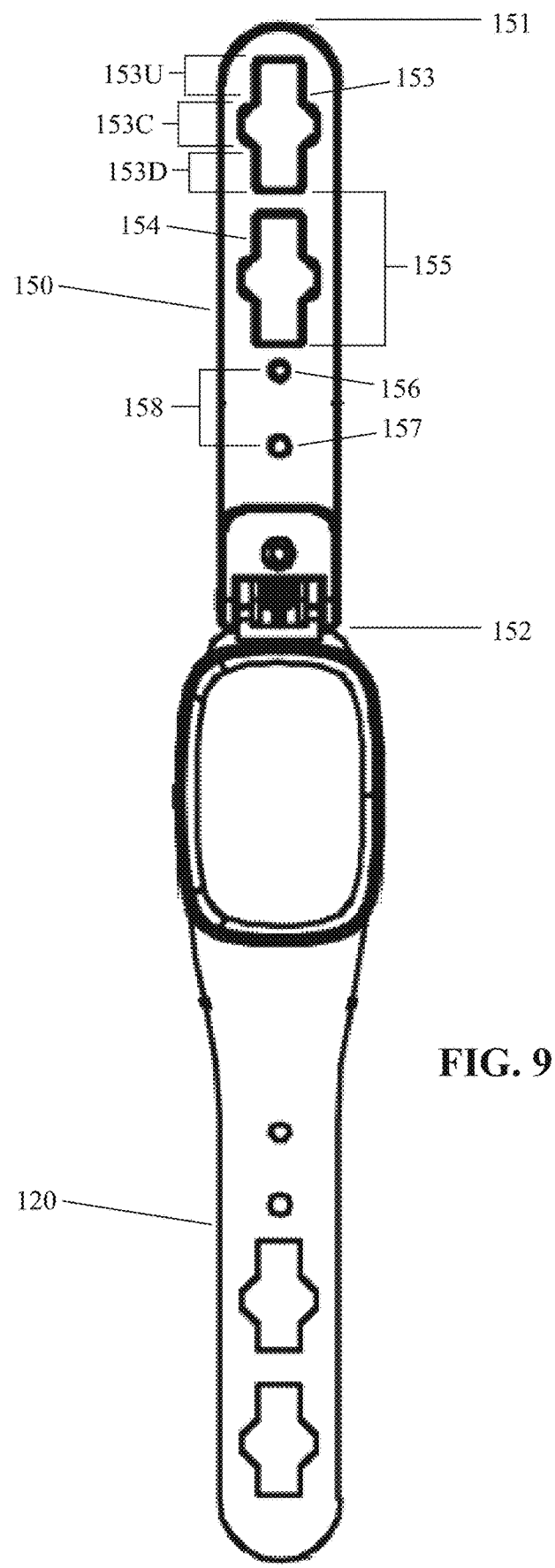
FIG. 9 is a side view of the upward extension member and lower extension member coupled together through a polycentric hinge and the worm drive arrangement.
Figure 11:
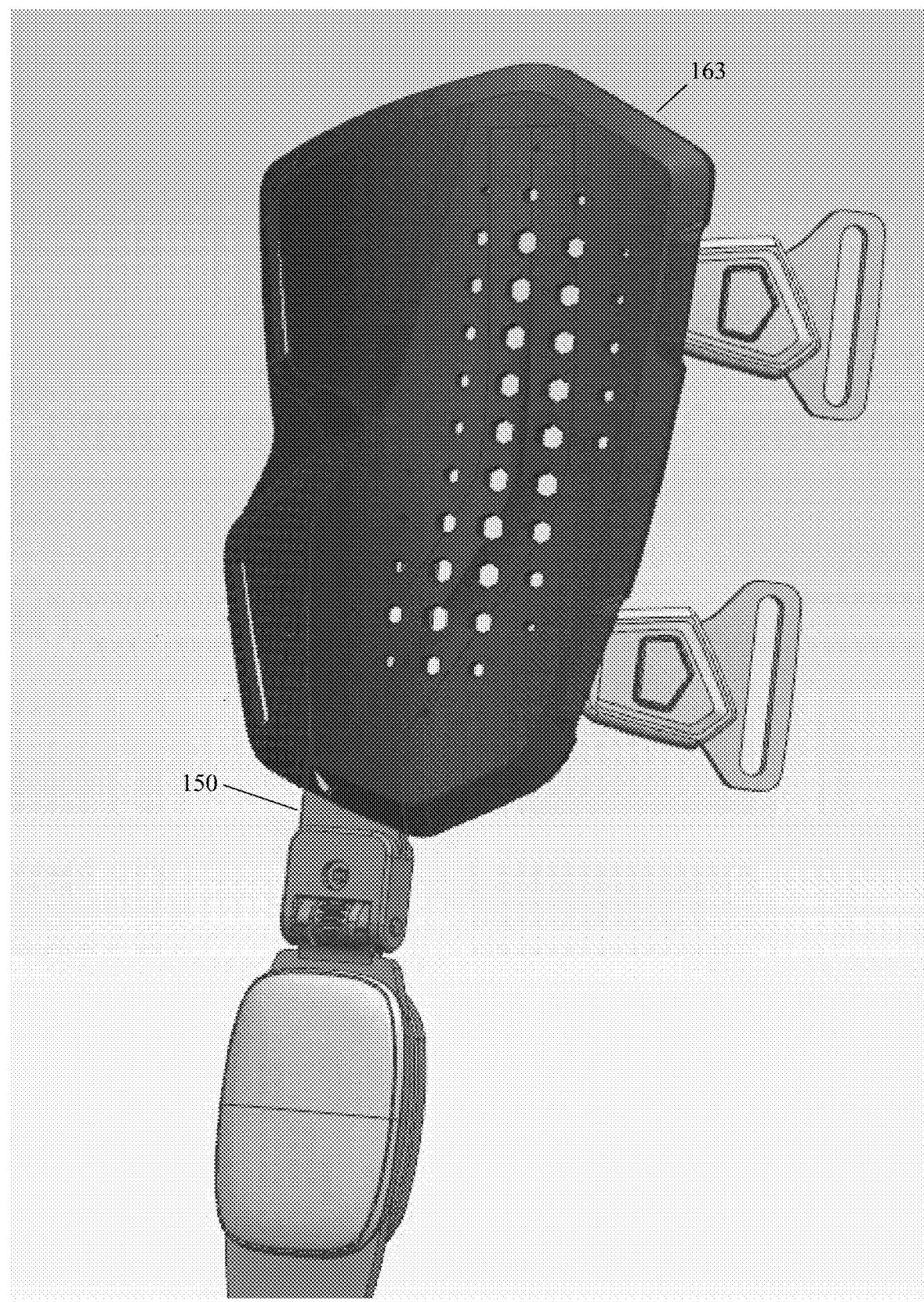
FIG. 11 is a reverse perspective view of the shell for the thigh pad, with the upper extension member releasably coupled thereto.

The opening(s) in the extension arms may be seen in isolation in FIG. 9. For the upper extension arm 150, a first cruciform-shaped opening 153 may be formed proximate to its first end 151, and a second cruciform-shaped opening 154 may be formed between the first end 151 and the second end 152, with a spacing 155 between the corresponding features of the openings. Each cruciform-shaped opening may be formed of a centrally positioned, horizontally disposed rectangular opening portion (e.g., 153C), with an upwardly disposed rectangular opening portion (e.g., 153U) and a downwardly disposed rectangular opening portion (e.g., 153D), each of which upwardly and downwardly disposed opening portions are narrower in width than the central opening portion 153C. As may be seen in FIG. 5, the upper shell 163 may be formed with only a single stud (e.g., 163A) where one opening is formed in the extension arm, or may instead be formed with a pair of studs (e.g., 163A and 163B) where the two cruciform-shaped opening are formed in the extension arm. As shown in more detail in FIGS. 10A, 10B, and 10C, each of the studs may be formed with a shank (e.g., shaft 163Bs) and a head (e.g., 163Bh) positioned at the end of the shaft, which may basically form a T-shaped stud with two legs, as shown therein. The shank 163S may have a width being slightly less than the width of the upwardly and downwardly disposed opening portions (153U and 153D), and the head 163Bh formed at the distal end of the shank 163Bs may have a periphery that is just slightly smaller than the central opening portion 153C, but wider than the width of each of the upwardly and downwardly disposed opening portions 153U and 153D.

Figure 16:
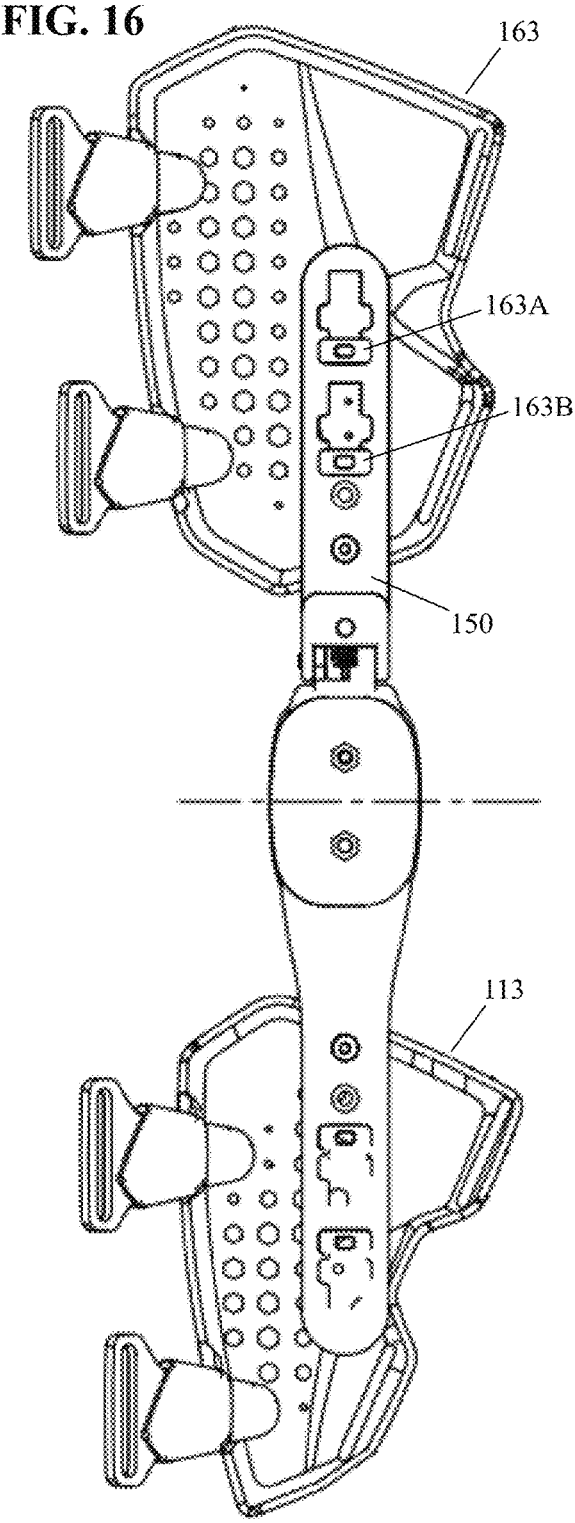
FIG. 16 is a side view showing the upper extension member releasably coupled to the shell for the thigh pad, and the lower extension member releasably coupled to the shell for the calf pad, shown with each of the extension members coupled to the shells at a first height-adjustable position.
Figure 17:
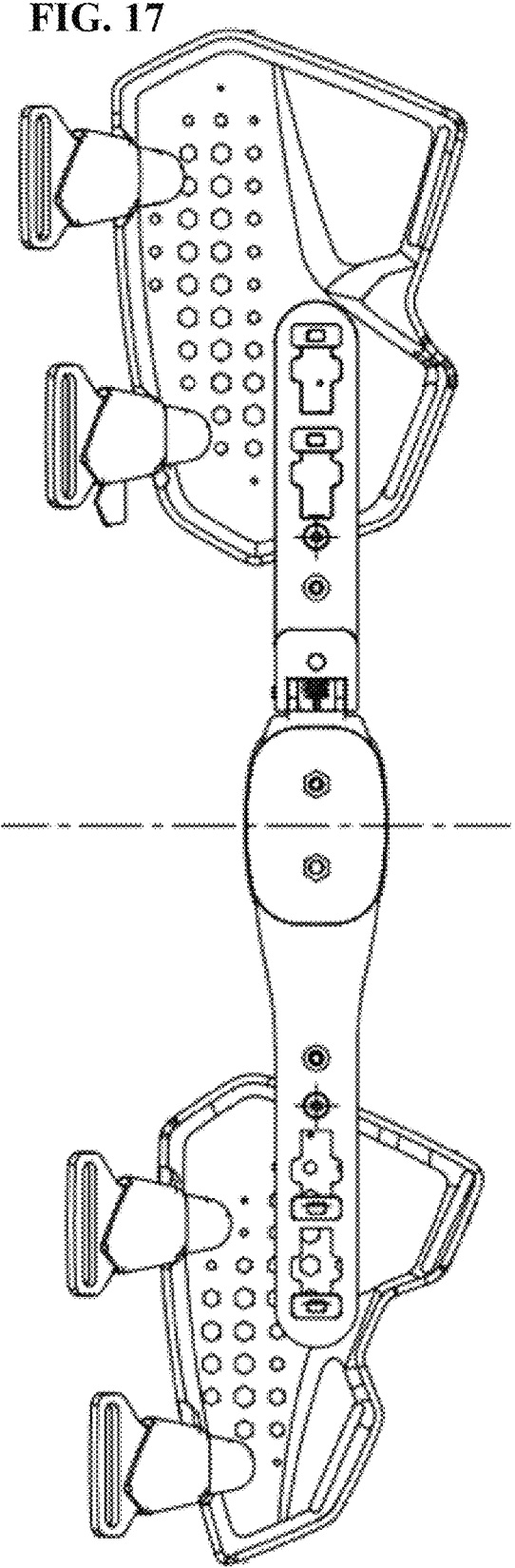
FIG. 17 is the side view of FIG. 16, but shown with each of the extension members coupled to the shells at a second height-adjustable position.

Thus, as may be seen from FIG. 10 and FIGS. 16-17, for joining of the upper extension arm 150 to the upper shell 163, the central opening portion(s) 153C of the two cruciform-shaped openings 153 and 154 of the extension arm may be positioned over the head(s) 163Bh, and the head(s) may be inserted therethrough. Next, depending upon the proportions of the wearer, the extension arm 150 may be slid upwardly to occupy the upwardly disposed rectangular opening portion 153U for a greater spacing with respect to the lower shell/pad for a taller wearer (see FIG. 17), or it may alternatively be slid downward into the downwardly disposed rectangular opening portion 153D for a smaller spacing with respect to the lower shell/pad for a shorter wearer (see FIG. 16).

To fixedly secure the upper extension arm 150 to the upper shell 163 at either location, a threaded insert 163I1 may be provided in the shell, and a pair of holes 156 and 157 may be formed in the extension arm being appropriately spaced apart a distance 158. So when the extension arm 150 is slid upwardly to occupy the upwardly disposed rectangular opening portion 153U for the greater spacing (FIG. 17), a screw may be inserted through the lower hole 157 and be rotated into engagement with the threaded insert 163I1. When the extension arm 150 is slid downward to occupy the downwardly disposed rectangular opening portion 153D for the smaller spacing (FIG. 16), the screw may be inserted through the upper hole 156 and be rotated into engagement with the threaded insert 163I1. The lower extension arm 120 may be coupled to the lower shell 113 in a similar manner.

The upper pad 164 and the lower pad 114 may each be formed of any suitable material known in the art, including, but not limited to, a rubber material, a plastic material, etc. In one embodiment the material for the pads may be a non-slip EVA (ethylene-vinyl acetate) material that may be molded into a curved or a compound curved shape to match the curvature of either the calf or a thigh. (Note that the shells may be respectively molded to match the curvature of either the calf or a thigh, or instead they may be flat, and the upper and lower pads may be thick enough to obviate the need for curvature in the shells). The periphery of the molded shape may also be wider at the top and narrower at the bottom as needed to hug the calf region.

Figure 12:
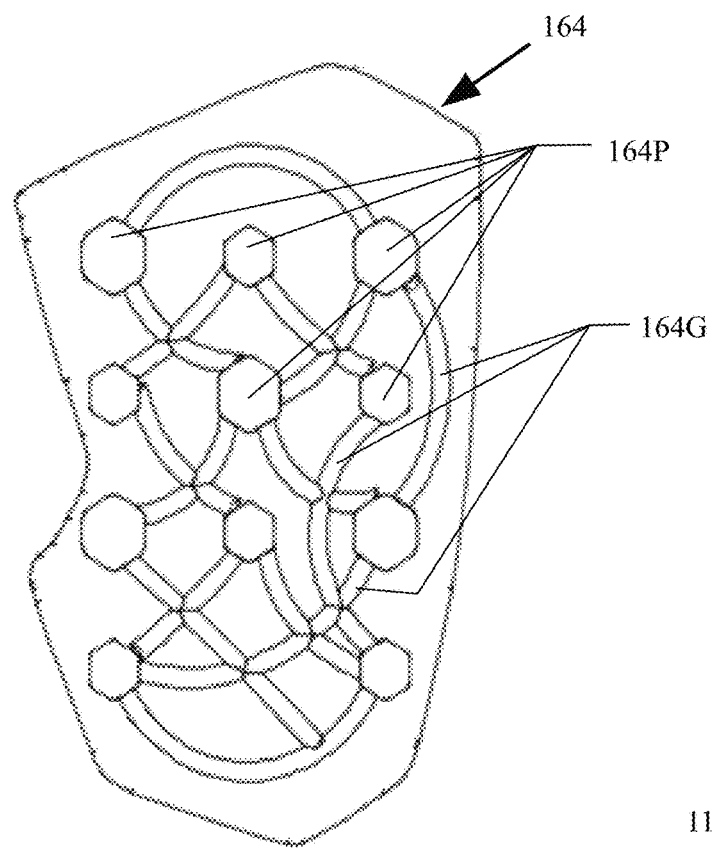
FIG. 12 is an enlarged side view of the inward facing side of the thigh pad.
Figure 13:
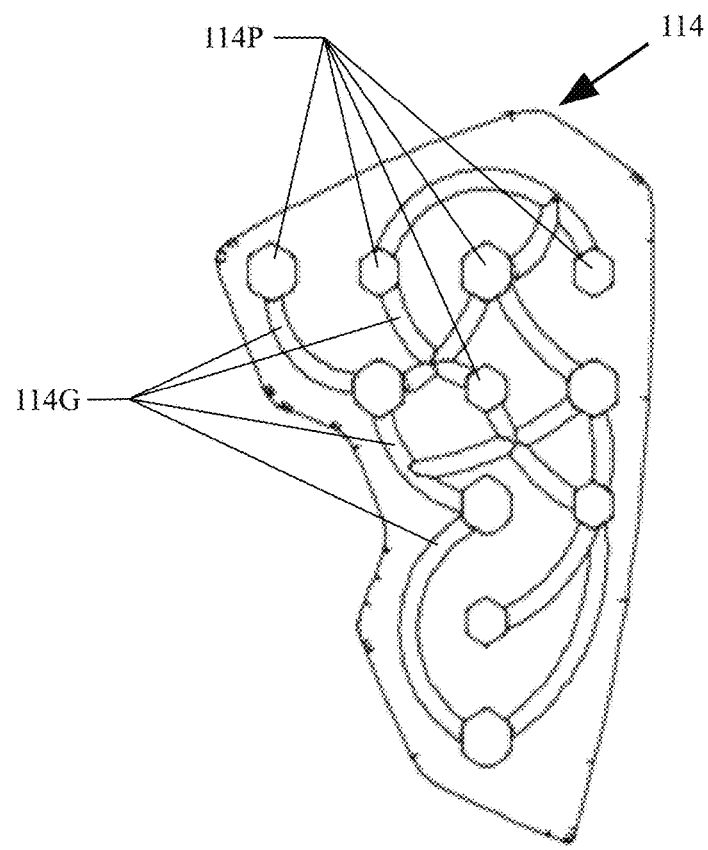
FIG. 13 is an enlarged side view of the inward facing side of the calf pad.
Figure 14:
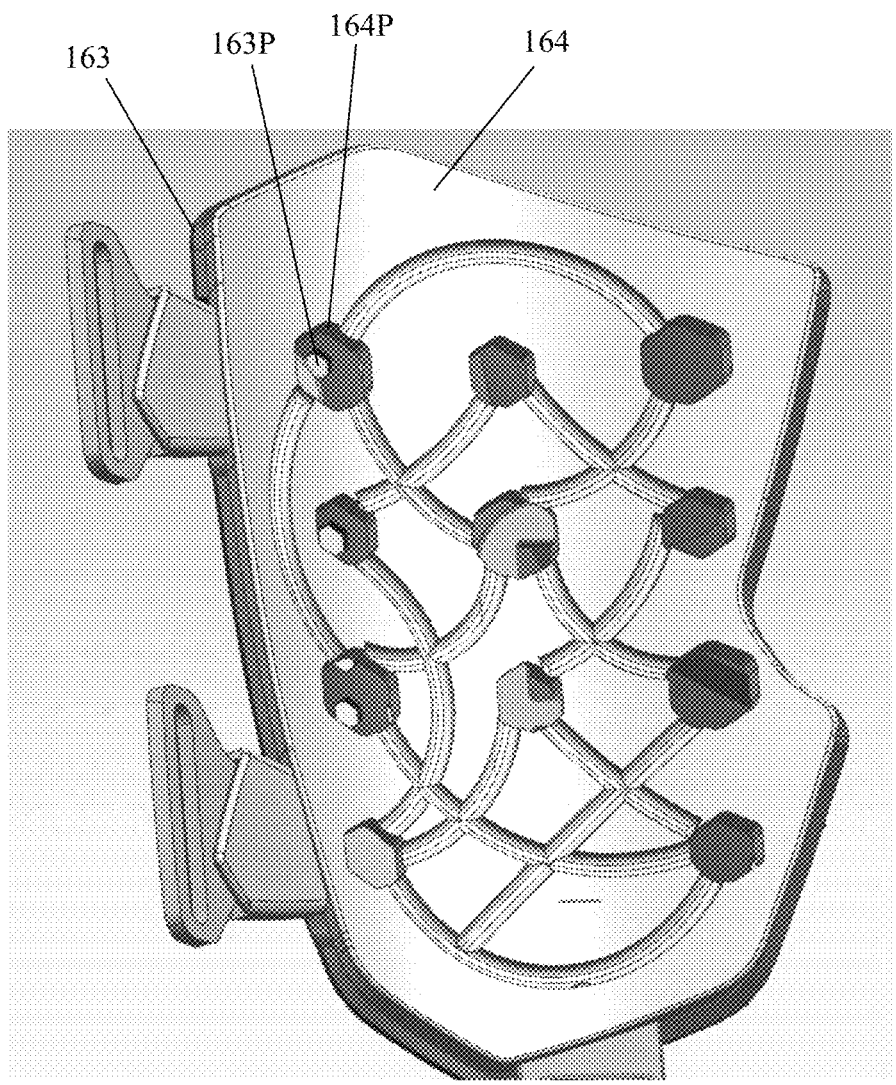
FIG. 14 is a side view showing the shell for the thigh pad with the upper extension member releasably coupled thereto, and with the thigh pad secured to the shell.
Figure 15:
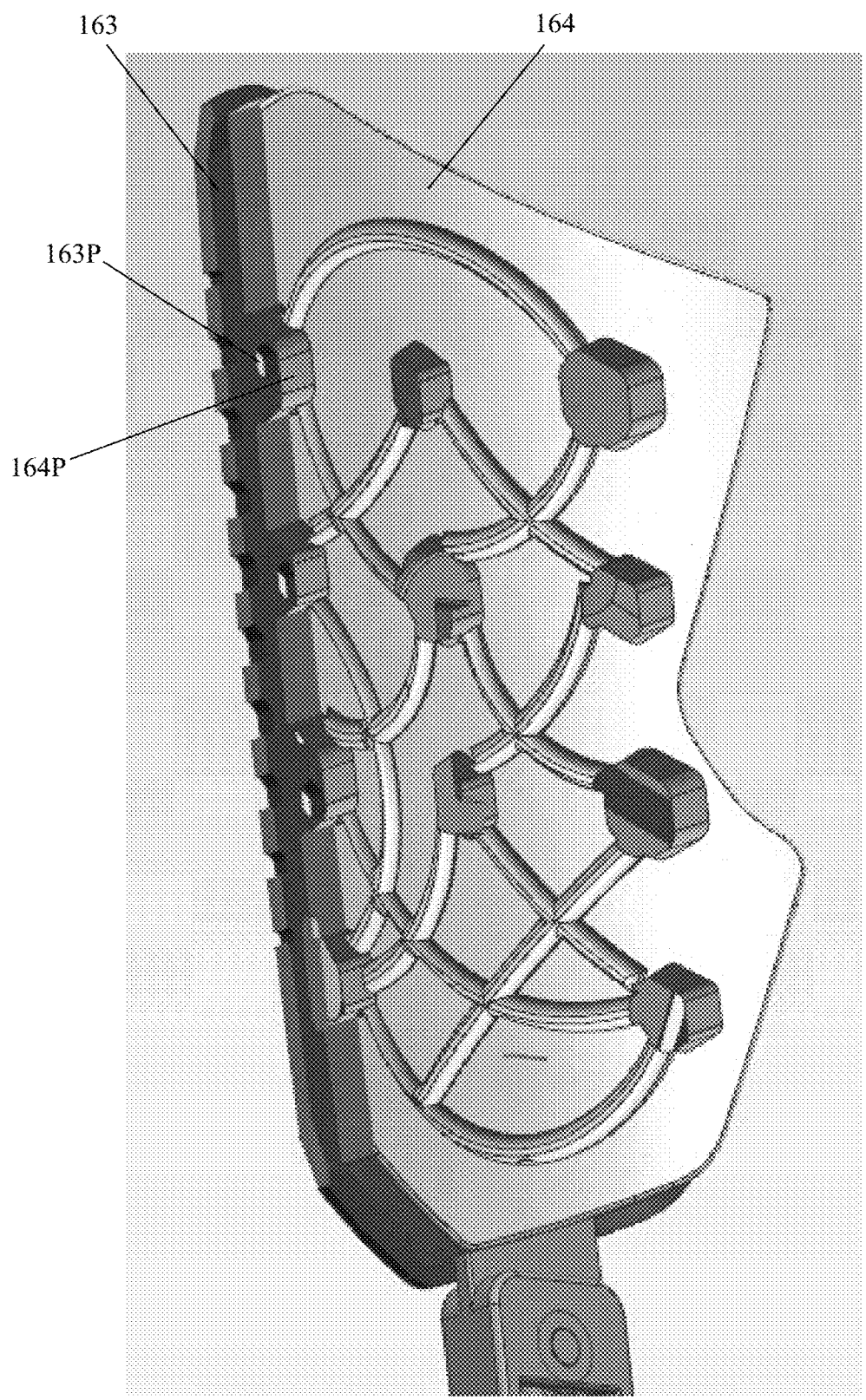
FIG. 15 is a section view of the arrangement of FIG. 14, showing openings in the thigh pad interconnected with openings in the shell.

The upper pad 164 and the lower pad 114 may each be formed with a respective plurality of ventilation openings 164P and 114P that may be equally spaced at least across a central surface area portion of the pad. In another embodiment, as seen in FIG. 12 and FIG. 13, alternate openings may be larger than the adjacent openings. At least a portion of the openings 164P and 114P in each of the upper pad 164 and the lower pad 114 may be positioned to interconnect with the corresponding openings 113P and 163P in the upper shell 113 and the lower shell 163 (see FIG. 14 and FIG. 15), as seen in FIG. 14. The openings interconnected between the shell and respective pad may provide a cooler arrangement for the pad of the brace 100 with respect to the wearer's leg by facilitating air circulation/movement and greater local heat transfer away from the person's body, while the wearer is moving and even while occupying a static position.

The upper pad 164 and the lower pad 114 may each also be formed with a respective plurality of grooves 164G and 114G, which grooves may run between each of the respective openings 164P and 114P in the upper pad 164 and the lower pad 114. As seen in FIG. 12 and FIG. 13, the openings and grooves, while being distributed in at least 80-90 percent the surface area of the pad (i.e., being distributed throughout the surface area of the pad, except near the periphery of the pad, which is distal from the straps). The pads being so formed with the plurality of openings 114P and grooves 114G for the lower pad 114, as well as the plurality of openings 164P and grooves 164G for the upper pad 164, also respectively serve to enable the pad to better grip the thigh/calf of the wearer, reducing the amount of tightening/tension required for the straps to properly secure the brace 100 to the wearer. The grooves may also better facilitate heat transfer. Because of the better gripping of the wearer's leg provided by the pad configuration disclosed herein, and the reduced tensioning required by the straps, the brace 100 is better able than prior art braces to be secured to the wearer without tending to cut off the blood flow locally through blood vessel beneath the pad(s) while it is being worn. The grip of the wearer's leg provided by the pad configuration disclosed herein also better adjusts to the increase and decrease in the calf/thigh surface perimeter changes during various different leg movements that contract and expand those muscles, and the pad configuration tends to better maintain its secured contact/placement on the leg even while the wearer is sweating.

The periphery of the upper pad 164 (and upper shell 163), and the periphery of the lower pad 114 (and lower shell 113) are each specifically shaped to keep the brace in its centered most point along a vertical line by which the joint operates through, and are not simply rounded plates as with prior art braces. The periphery, and the portion of the upper pad 164 (and upper shell 163) that have the openings and grooves, form roughly an elongated rectangular shape. The periphery, and the portion of the lower pad 114 (and lower shell 113) that have the openings and grooves, form roughly a triangular shape.

The upper pad 164 may be secured to the upper shell 163 in any manner known in the art, including, but not limited to the use of adhesive. In one embodiment, the upper pad 164 may be releasably coupled to the upper shell 163 using hook and loop fastening materials sold under the trade name of "Velcro." Such releasable coupling may permit removal of the upper pad 164 to accommodate adjusting of the position of the upper extension arm 150 with respect to the upper shell 163 using the pair of studs 163A and 163B.

Figure 36:
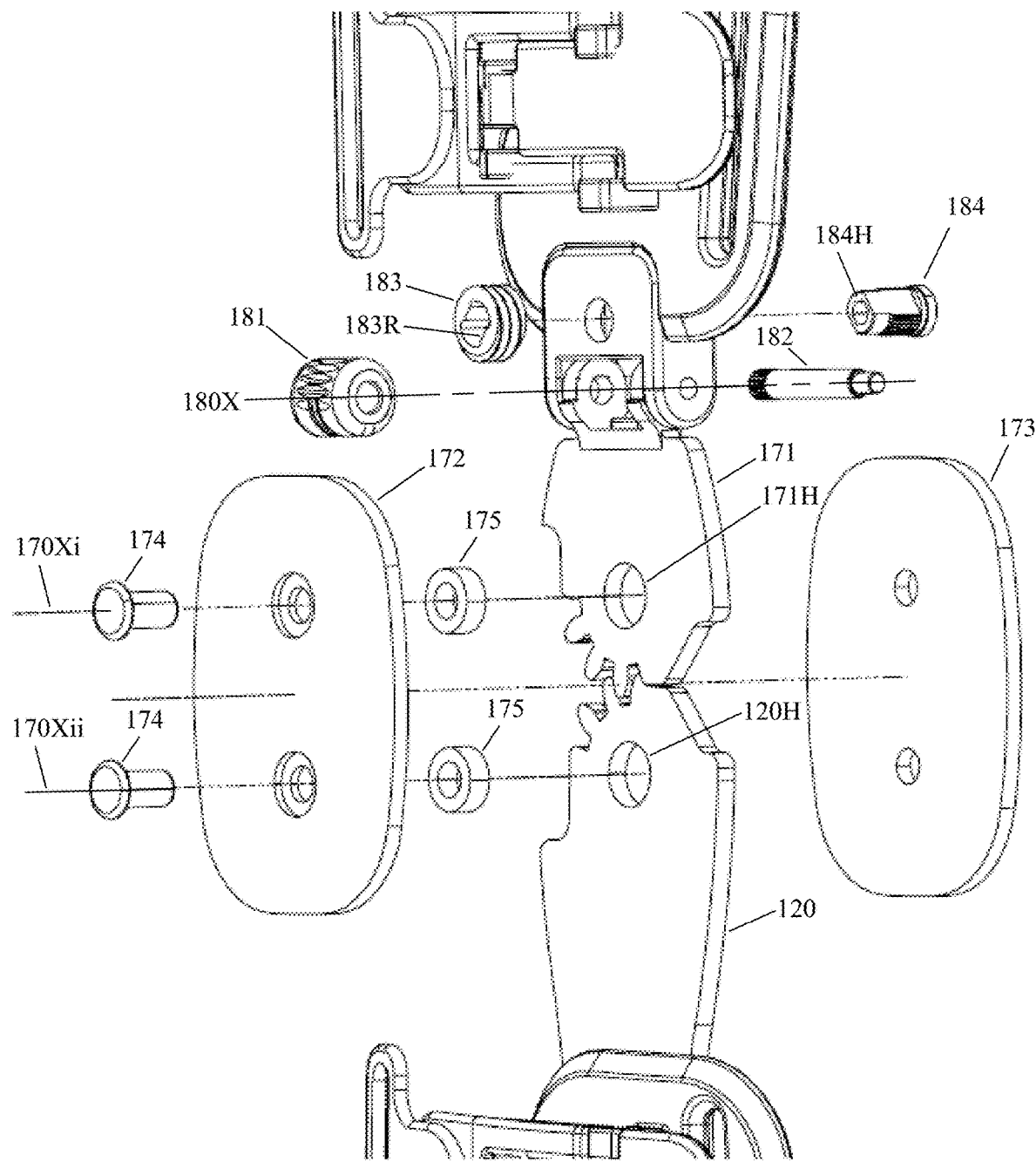
FIG. 36 is an exploded view of the component parts of the polycentric hinge arrangement and the worm drive arrangement.
Figure 37:
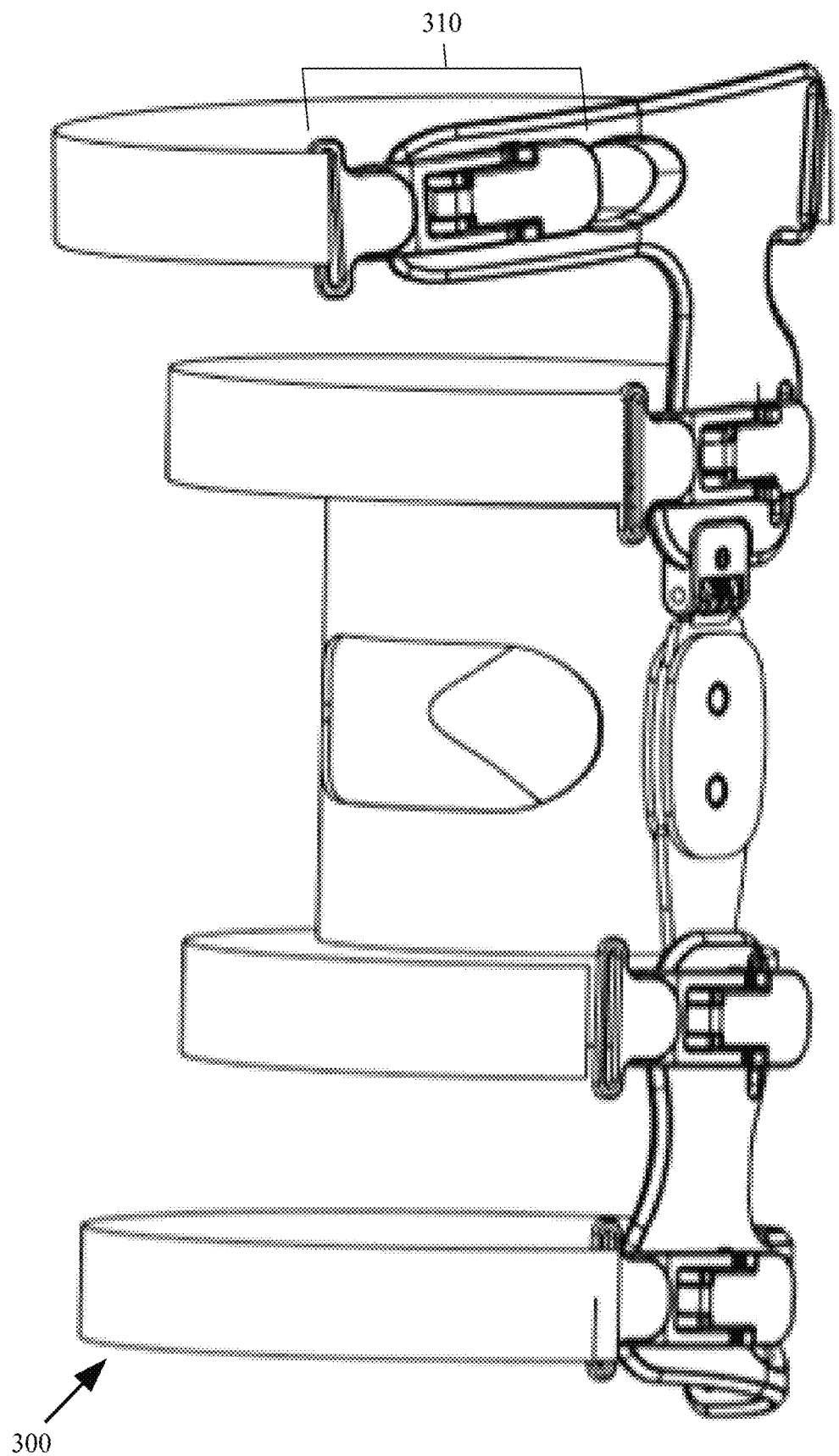
FIG. 37 is a perspective view of a third embodiment of a knee brace as disclosed herein.
Figure 39:
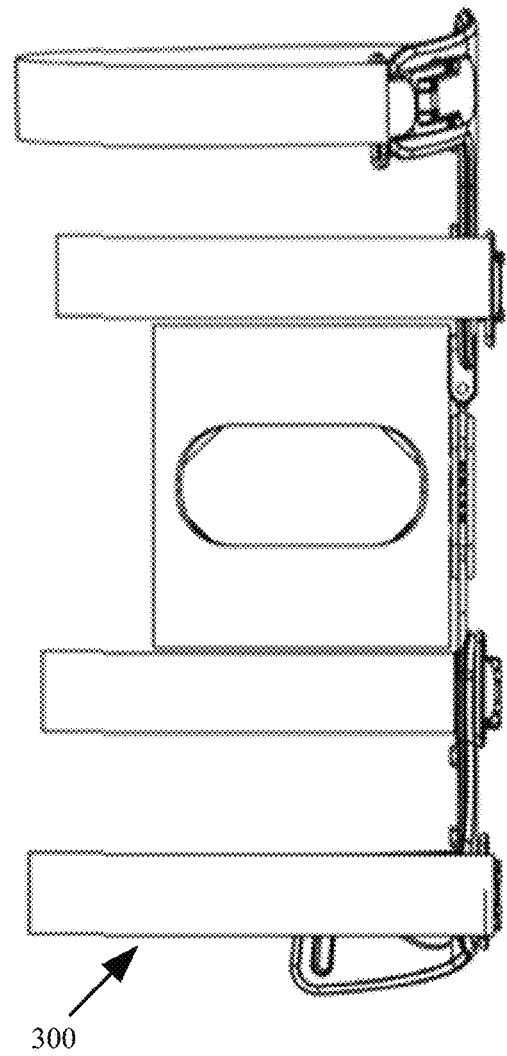
FIG. 39 is a side view of the knee brace shown in FIG. 37.
Figure 38:
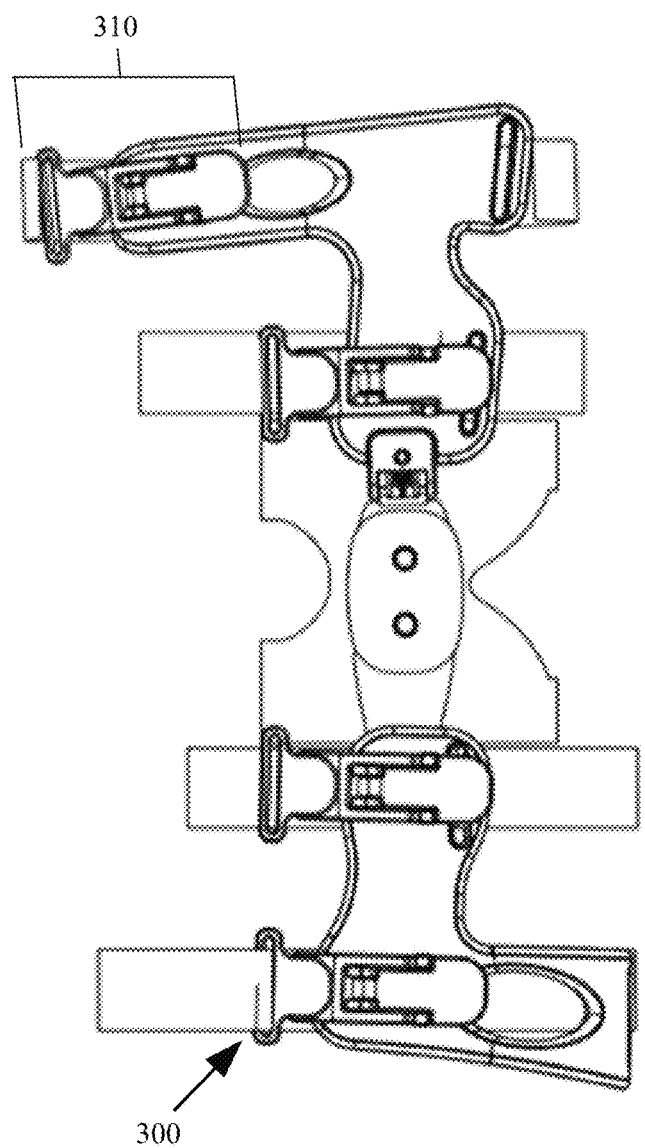
FIG. 38 is a front view of the knee brace shown in FIG. 37.
Figure 40:
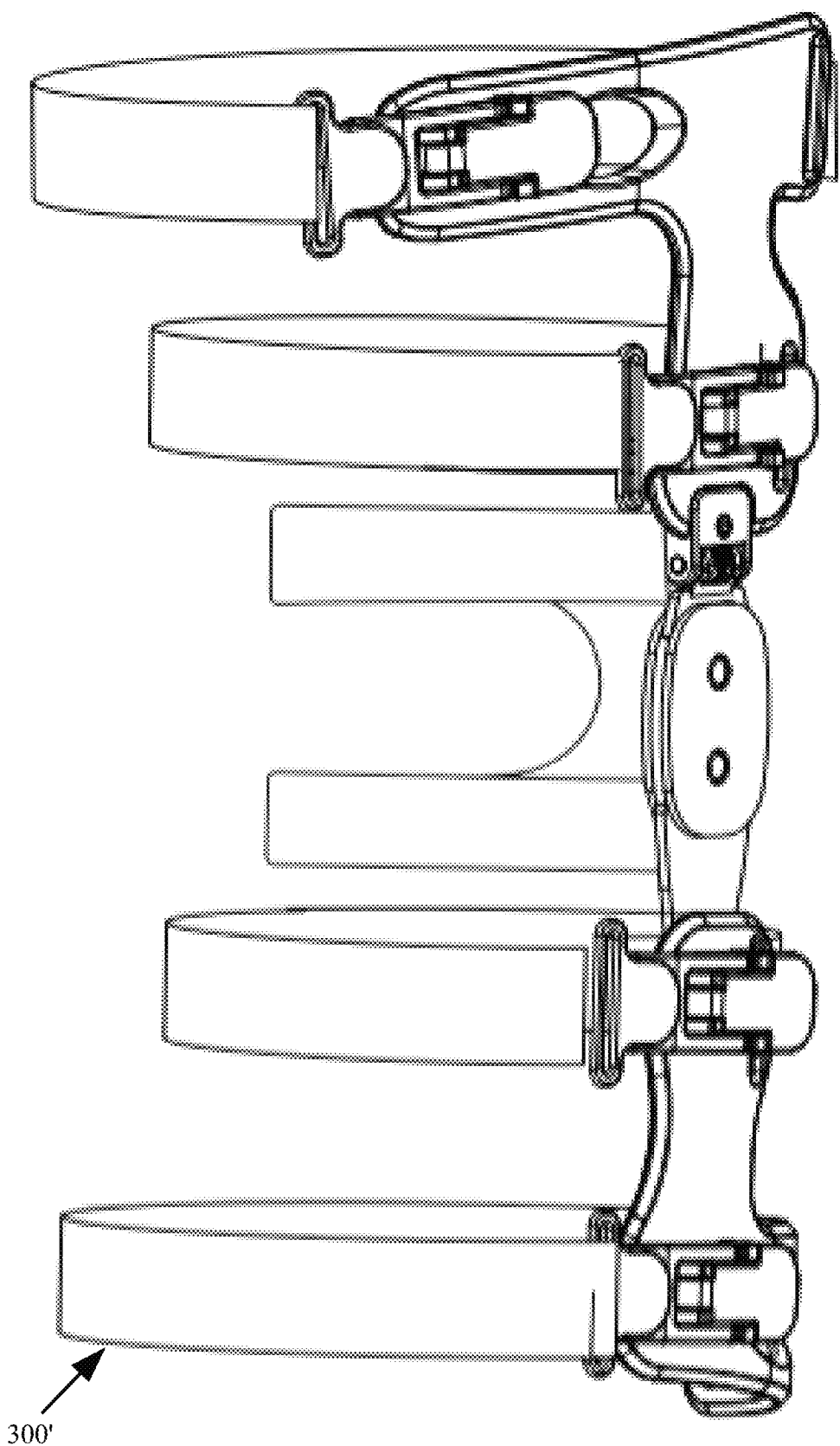
FIG. 40 is a perspective view of a fourth embodiment of a knee brace as disclosed herein.
Figure 42:
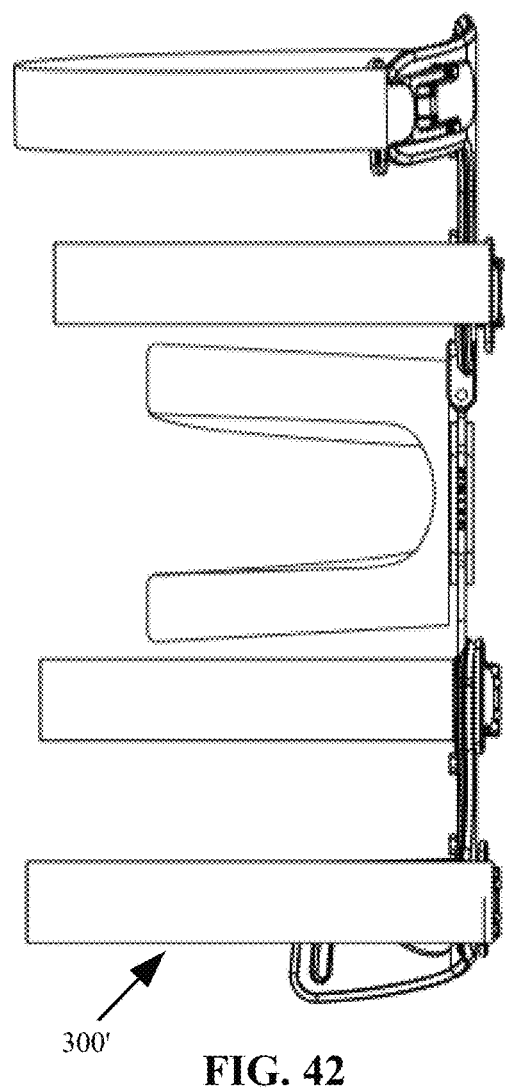
FIG. 42 is a side view of the knee brace shown in FIG. 40.
Figure 41:
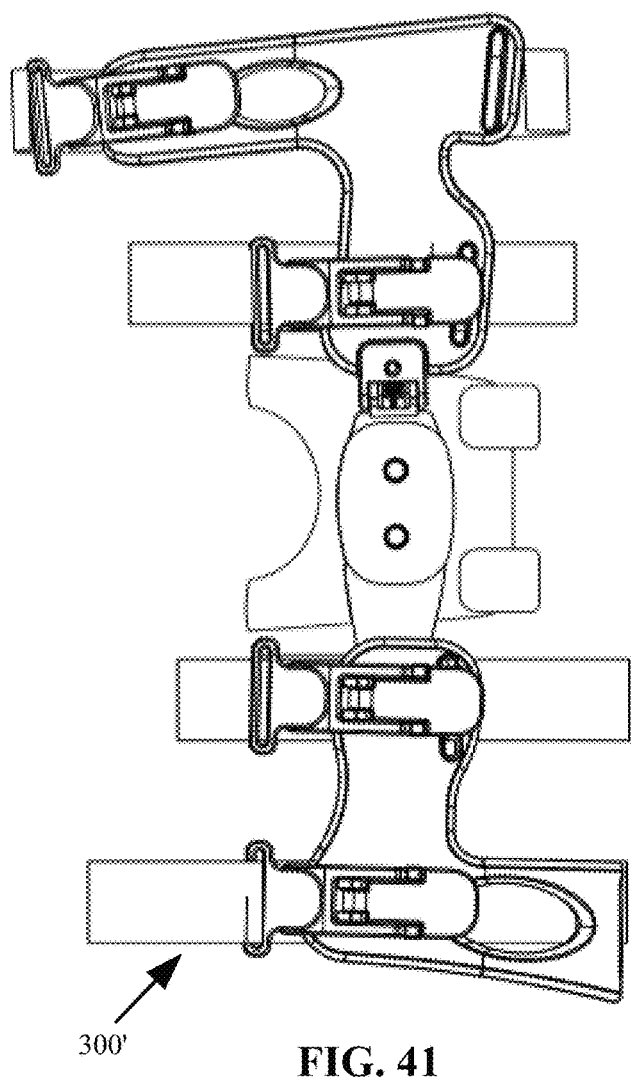
FIG. 41 is a front view of the knee brace shown in FIG. 40.

As seen in FIG. 5 and FIG. 36, the upper extension arm 150 may be coupled to the lower extension arm 120 via a bicentric hinge assembly and the worm drive arrangement.

The bicentric hinge arrangement 170 may permit rotational movements of the lower cuff assembly 110 with respect to the upper cuff assembly 150 about first and second rotational axes 170Xi and 170Xii. The bicentric hinge 170 may include a hinge hole 120I1 formed in the lower extension arm 120, and a hinge hole 171H formed in a hinge plate 171. Relative pivotal movement may be provided by a pair of face plates 172 and 173 having correspondingly positioned holes to receive mechanical fasteners (e.g., rivets) through the hinge holes. The manufactured head and the bucked head of the rivets may each be countersunk within recesses formed in the face plates 172 and 173. To protect against galling of the holes 120I1 and 171H in the extension arm 120 and the hinge plate 171, respectively, appropriately sized bushings 175 may be inserted into those holes (e.g., in an interference fit) prior to assembly of the brace. The bushings 175 may be made of any suitable material, including, but not limited to bronze. The bushings 175 may also be slightly longer in length than the thicknesses of the extension arm 120 and the hinge plate 171, which may be the same thickness, so that the face plates 172 and 173 when riveted together bear up against the bushings and not against the extension arm 120 and the hinge plate 171, which otherwise may cause binding of those members that would inhibit rotational movements. Also, to assure the same relative rotation of both the extension arm 120 and the hinge plate 171 with respect to the face plates, each may be formed to include a respective plurality of gear teeth 172G and 120G, which respective gear teeth may mesh together. Therefore, when either of the extension arm 120 or the hinge plate 171 rotates/pivots with respect to the face plates, the other member must also rotate/pivot synchronously as a result of the geared connection.

The worm drive arrangement 180 may permit lateral rotational adjustments to the relative angle between the upper and lower cuffs about axis 180X, which may be substantially perpendicular to the rotation axes 170Xi and 170Xii. The worm drive arrangement 180 may include a clevis formed on the upper end of the hinge plate 171, a clevis formed on the lower end of the upper extension arm 150 by a first lug 171Li and a second lug 171Lii (FIG. 19), a worm gear/wheel 181, a mounting pin 182 for rotatable coupling of the clevis of the hinge plate to the extension arm clevis and for supporting of the worm gear/wheel between the lugs 171Li and 171Lii of the hinge plate clevis, a worm screw 183, and a mounting pin 184 for rotatable mounting of the worm screw to the upper extension arm.

Figure 18:
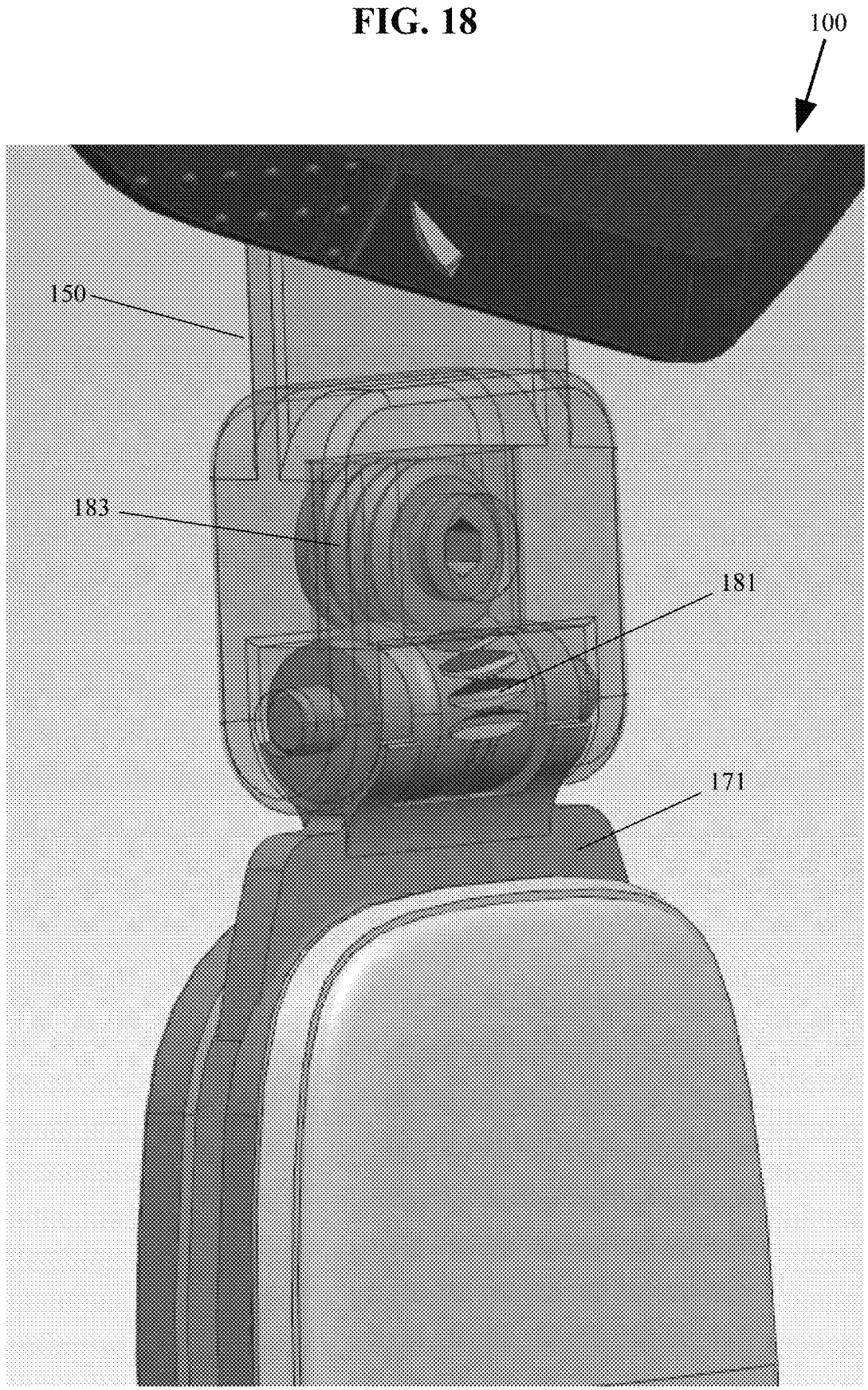
FIG. 18 is a transparent view showing the worm drive arrangement enclosed within a casing.
Figure 19:
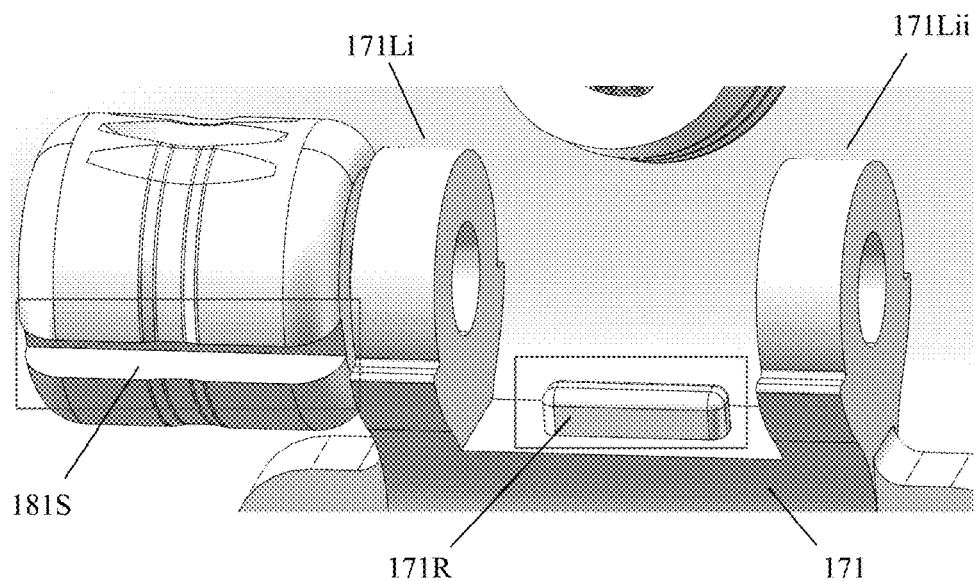
FIG. 19 is an exploded view showing the worm gear wheel rotated to expose an axial slot, being positioned adjacent to the mounting clevis on the upper hinge plate.
Figure 20:
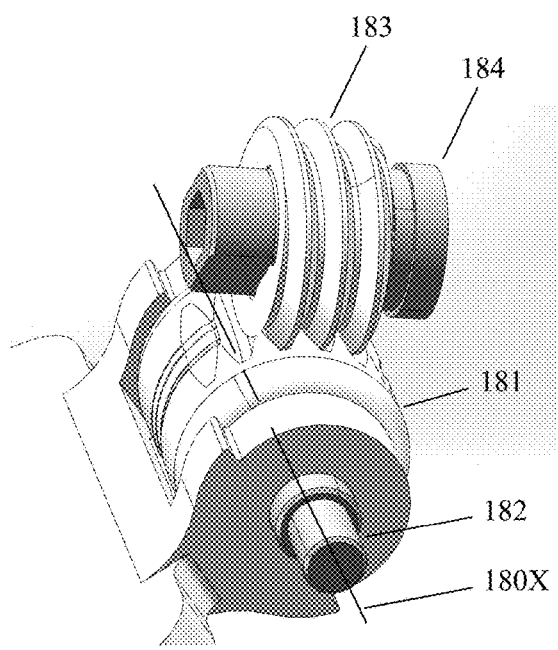
FIG. 20 is a first perspective view of the worm wheel pivotally coupled to the clevis of the upper hinge plate, and shown with the worm screw engaged with the worm gear wheel to form the worm drive arrangement.
Figure 21:
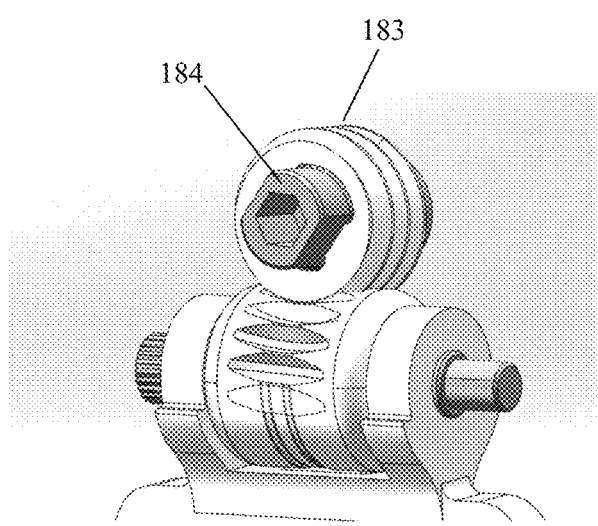
FIG. 21 is a second perspective view of the worm wheel pivotally coupled to the clevis of the upper hinge plate.
Figure 22:
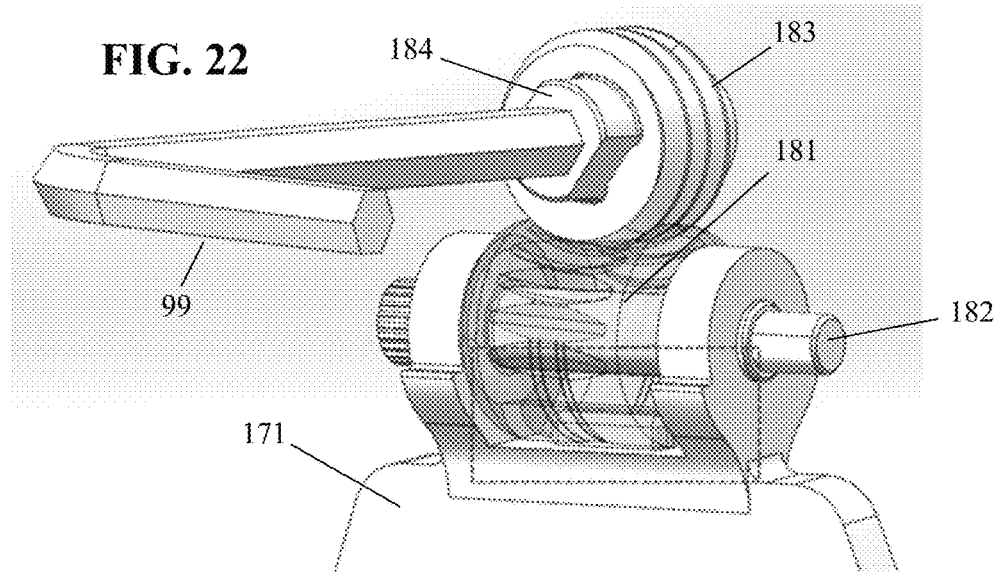
FIG. 22 is a third perspective view of the worm gear wheel pivotally coupled to the clevis of the upper hinge plate of the polycentric hinge, with the worm screw engaged with the worm gear wheel, and shown with an Allen wrench engaged with the worm screw to rotatably adjust the lateral angle between the upper and lower extension arms of the knee orthosis.

The worm gear/wheel 181 is shown in detail in FIGS. 30-33. The worm gear/wheel 181 may be formed to include a plurality of gear teeth 181G that may be created by a corresponding plurality of recesses in the outer periphery of the generally cylindrical wheel. In one embodiment, the plurality of gear teeth 181G may be seven to eight teeth. However, in a preferred embodiment, there would be at least nine gear teeth 181G to permit better adjustability for the brace. A mounting hole 181I1 may be formed along the axis 181X of the cylindrical wheel, and a slot 181S beginning at the exterior surface of the worm gear/wheel 181 and extending to a depth 181D may be formed to be parallel to the axis 181X. The worm gear/wheel 181 may be formed with a diameter D and a length L. As seen in FIG. 19, the first lug 171Li and the second lug 171Lii of the clevis of the hinge plate 171 may be spaced apart a distance slightly greater than the length L of the worm gear/wheel 181. Also, the hinge plate 171 may be formed with a protrusion 171R between the lugs of the clevis, which protrusion may be received within the slot 181S of the worm gear/wheel 181 when the hinge plate 171 and the worm gear/wheel is mounted with respect to the clevis of the upper extension arm 150 using the mounting pin 182 (see FIG. 18 and FIG. 22).

Figure 23:
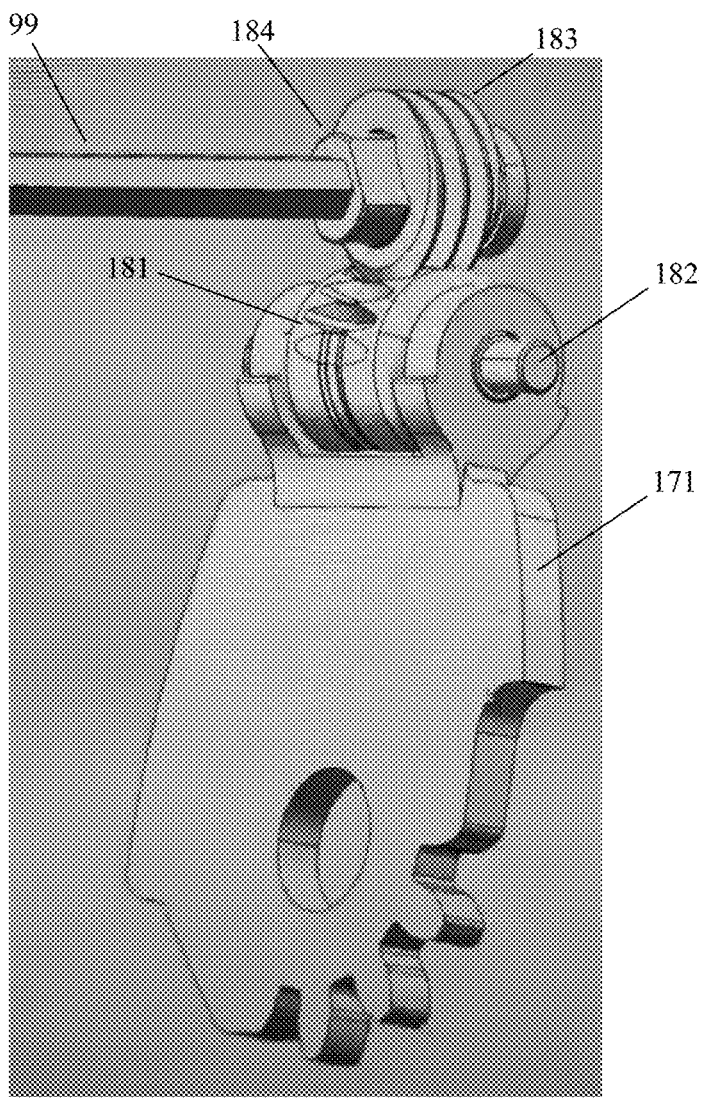
FIG. 23 is a fourth perspective view of the worm gear wheel pivotally coupled to the clevis of the upper hinge plate, with the worm screw engaged with the worm gear wheel, and shown with the Allen wrench still engaged with the worm screw after having rotatably adjusted the lateral angle between the upper and lower extension arms.
Figure 24:
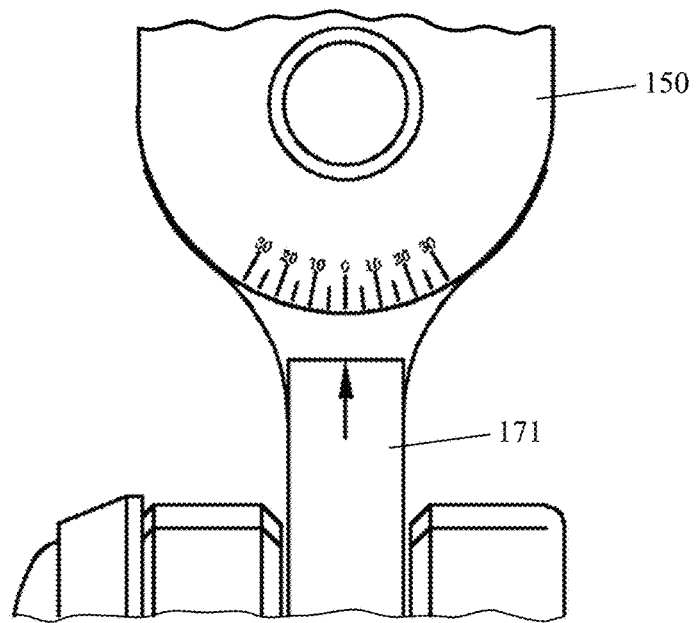
FIG. 24 is a side view showing the upper hinge plate of the polycentric hinge after being adjusted/rotated to be at an angle with respect to the upper extension arm.

The worm screw 183 is shown in detail in FIGS. 26-29. The worm screw 183 may be formed to include a helical screw thread 183T configured to mesh with the plurality of gear teeth 181G of the worm gear/wheel 181 when the worm screw is mounted transversely within the recess of the upper extension arm 150, and the worm gear is driven to rotate. The worm screw 183 may be formed with a slotted axial recess 183R that may receive the correspondingly shaped shaft of the pin 184 therein (see FIG. 36), and the pin 184 may be formed to include a recess 184R (e.g., having a recess with a hexagonal cross-section), which recess may be configured to receive a tool therein (e.g., an Allen wrench 99), so that rotation of the tool causes lateral rotational adjustments to the relative angle between the upper and lower cuffs about axis 180X (see FIGS. 22-23). Since the worm gear/wheel 181 is maintained in a static position with respect to the hinge plate 171 because of the engagement of the protrusion 171R within the slot 181S of the worm gear/wheel 181, rotation of the tool causes rotational movement of the worm screw 183 and thus rotational movement of the upper cuff with respect to the axis 180X.

Figure 25:
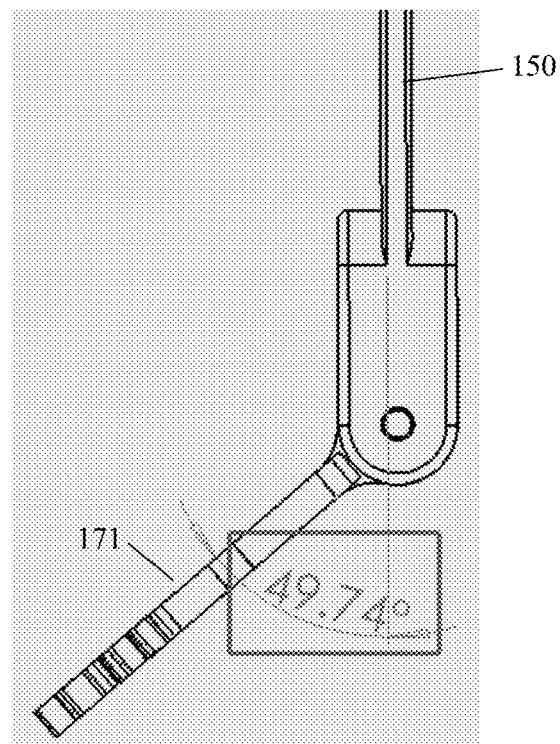
FIG. 25 is a side view of the worm drive arrangement showing a measurement scale and arrow indicator marking to indicate the current adjustment angle between the upper and lower extension arms provided by the worm drive arrangement.
Figure 26:
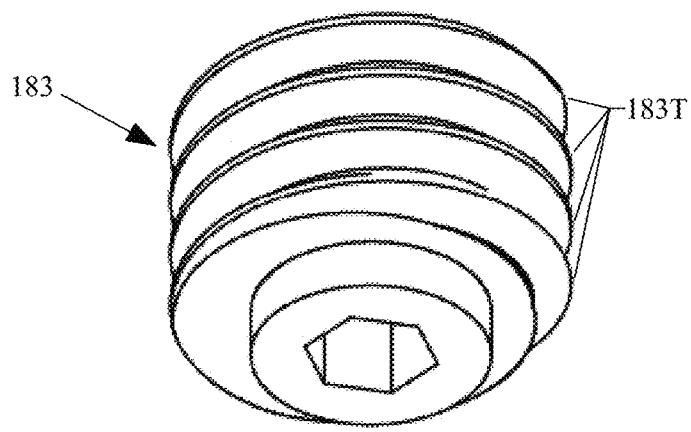
FIG. 26 is an enlarged perspective view of the worm screw of FIGS. 20-23.
Figure 28:
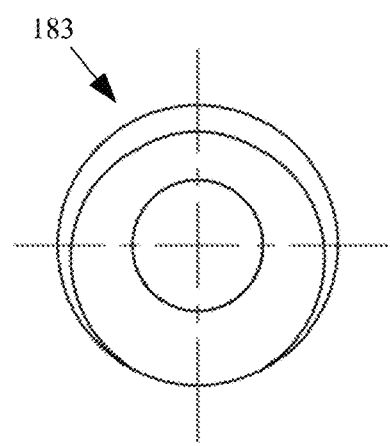
FIG. 28 is a top view of the worm screw of FIG. 26.
Figure 27:
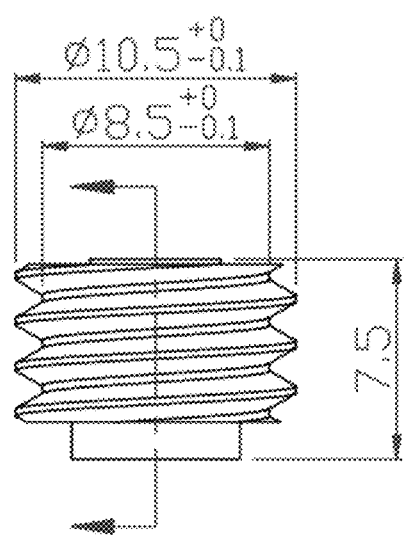
FIG. 27 is a side view of the worm screw of FIG. 26.
Figure 29:
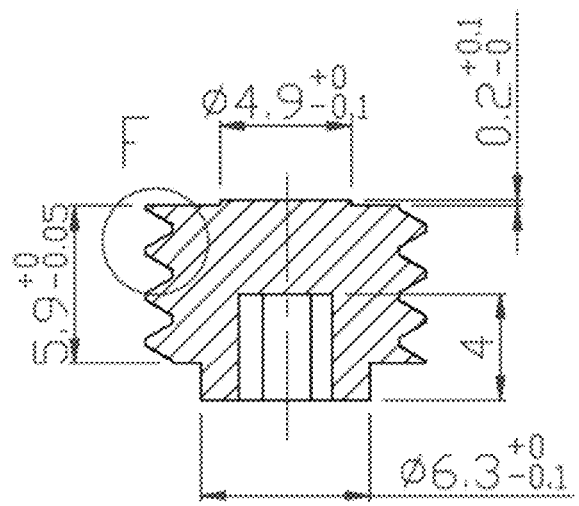
FIG. 29 is a cross-sectional view through the worm screw of FIG. 26.
Figure 30:
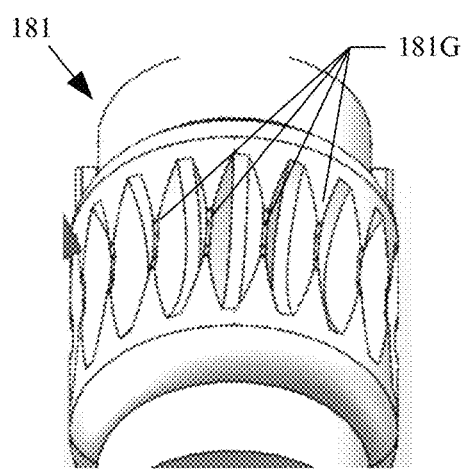
FIG. 30 is a enlarged perspective view of the worm wheel of FIGS. 20-23.
Figure 31:
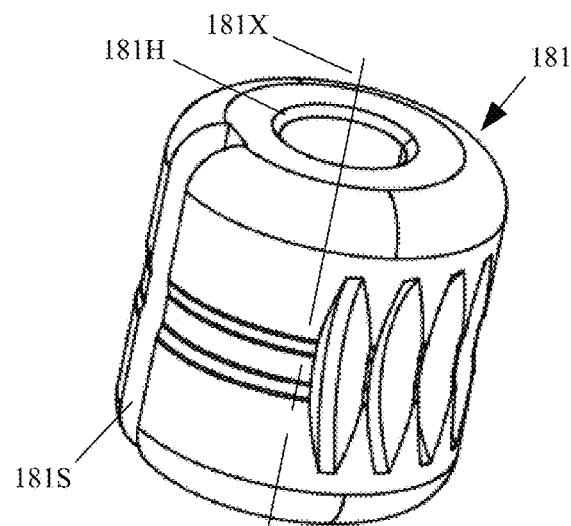
FIG. 31 is a second perspective view of the worm wheel of FIG. 30.
Figure 32:
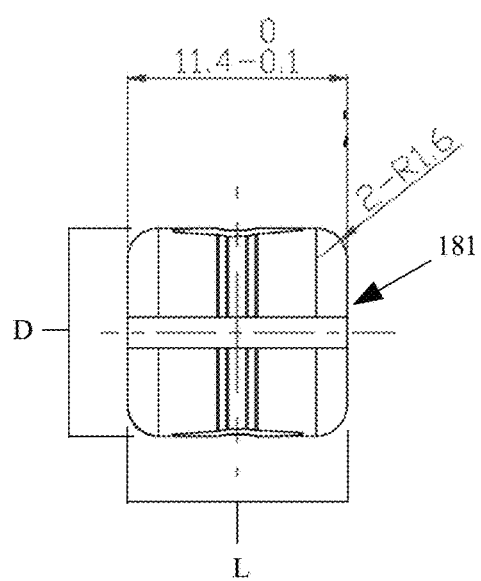
FIG. 32 is a front view of the worm gear wheel of FIG. 30.
Figure 33:
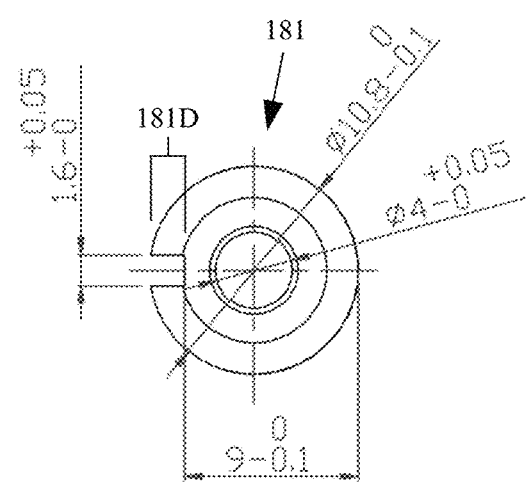
FIG. 33 is a side view of the worm gear wheel of FIG. 30.

As seen in FIG. 25, the upper extension arm 150 may have a plurality of angular degree markings formed thereon (e.g., "0"; "10", "20", etc.), and the hinge plate 171 may be formed with an indicator marking (e.g., and arrow), which may be used to provide an outward indication to the wearer or to the wearer's physician, as to the relative angle at which the lower cuff has been rotationally adjusted with respect to the upper cuff.

Figure 5A:
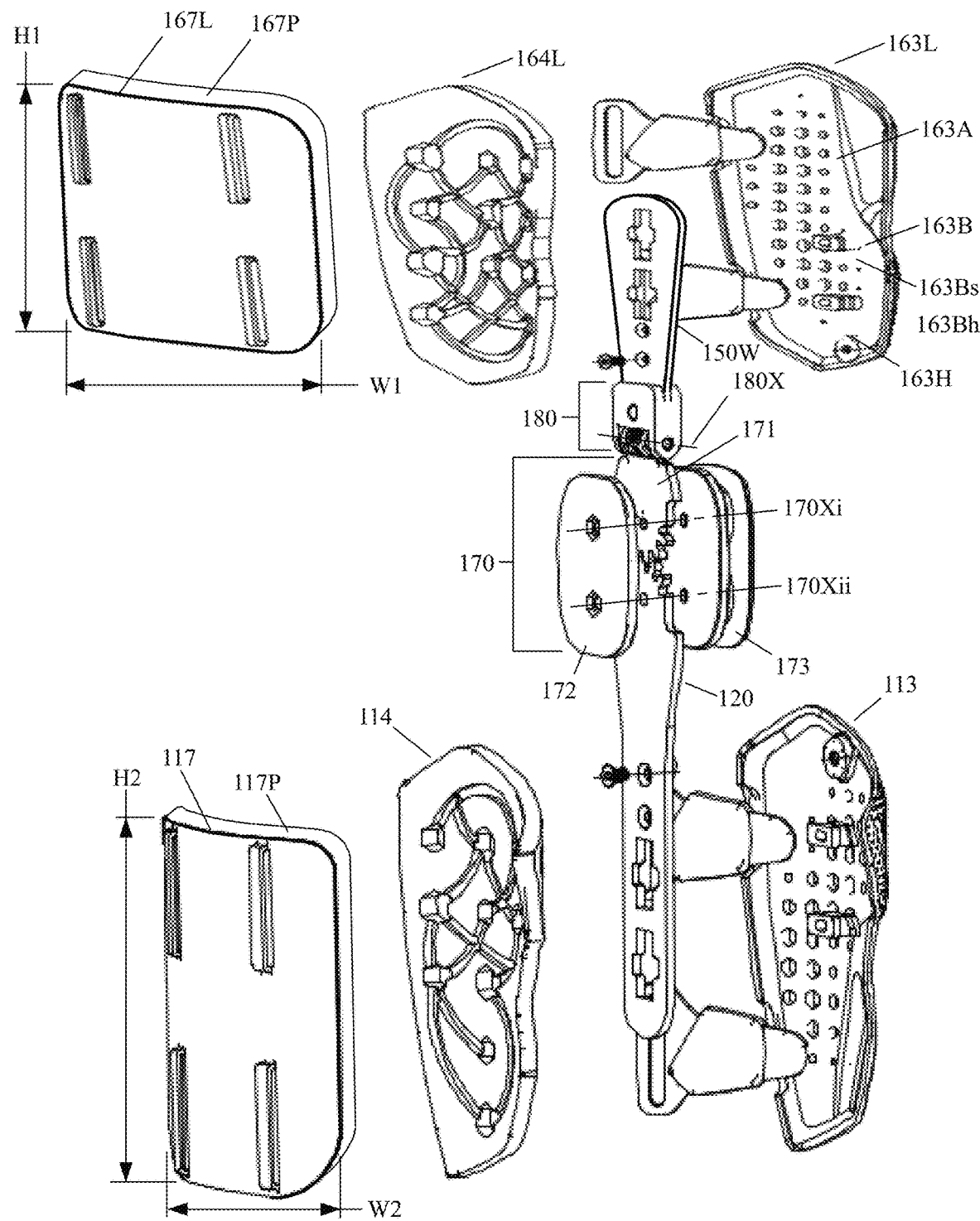
FIG. 5A is an exploded view of the larger component parts of a different version of the knee brace of FIG. 1.
Figure 6:
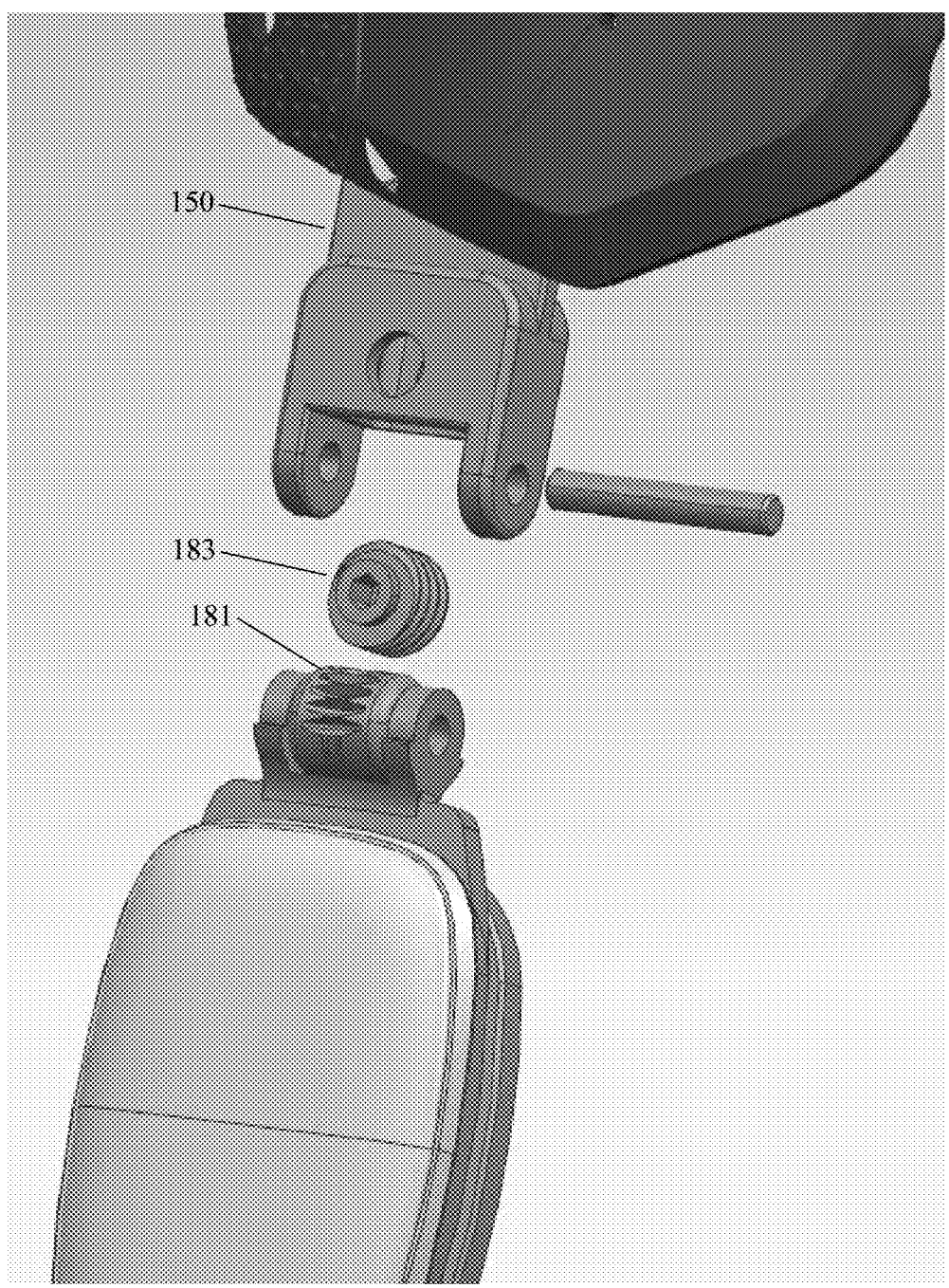
FIG. 6 is an exploded view of the component parts of a worm drive arrangement used for the knee brace of FIG. 1.

A different version of knee brace 100 may be formed as a brace 100' using most of the same components parts, but with some slight differences that may be seen in FIG. 5A. As seen in FIG. 5A, the knee brace 100' may be formed with an upper contact plate 167L that may have a reduced height, such that its width W1 is greater than its height H1, whereas the lower contact plate 117 may have a height 112 that is greater than its width W2. In one embodiment, the ratio of the width W1 to the height H1 may be between 1.1 and 1.2, and in another embodiment it may be between 1.2 and 1.4, and in yet another embodiment it may be between 1.4 and 1.6, and in other embodiments, any combination of those ratios or other ratios may alternatively be used. The ratio of the height 112 to the width W2 of the lower contact plate 117L may be formed with the same or similar ratios for various different embodiments. With the proportions of upper contact plate 167L being so formed, it is configured to achieve a hamstring-quad hold on the wearer's leg, and with the proportions of the lower contact plate 117 being so formed, it is configured to achieve a calf hold. The knee brace 100' may also be formed with a respective pad (i.e., pad 117P and pad 167P) being secured to the lower contact plate 117 and the upper contact plate 167L, which pads 167P and pad 117P may be formed the same as pads 164 and 114 with its plurality of ventilation grooves 164G/114G that run between the respective openings 164P/114P. The pad 117P of the lower contact plate 117 may thus act in combination with the pad 114 on the opposite side of the wearer's calf to better grip the leg without reducing blood flow to the calf attachment area. Similarly, the pad 167P of the upper contact plate 167L may thus act in combination with the pad 164 on the opposite side of the wearer's thigh to better grip the leg without reducing blood flow to the thigh attachment area. To accommodate higher loads (e.g., torque) at the thigh attachment area, the upper extension arm 150W may be formed to be much wider at is distal end (compare upper extension atm 150W in FIG. 5A with upper extension arm 150 in FIG. 5).

Figure 18A:
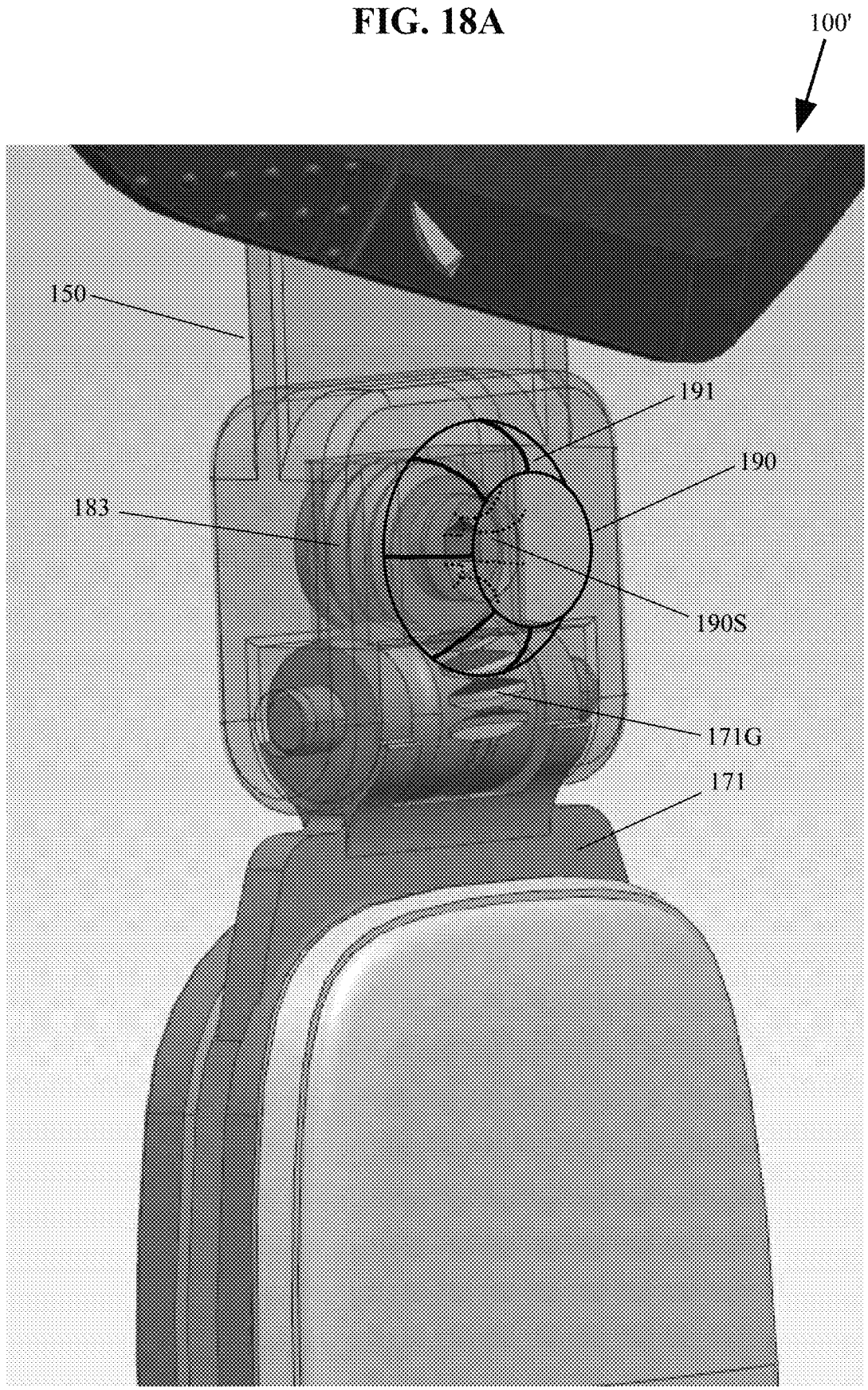
FIG. 18A is the transparent view of FIG. 18, but showing another version of the worm drive arrangement that includes an exterior knob for making lateral rotational adjustments to the relative angle between the upper and lower cuffs.
Figure 18B:
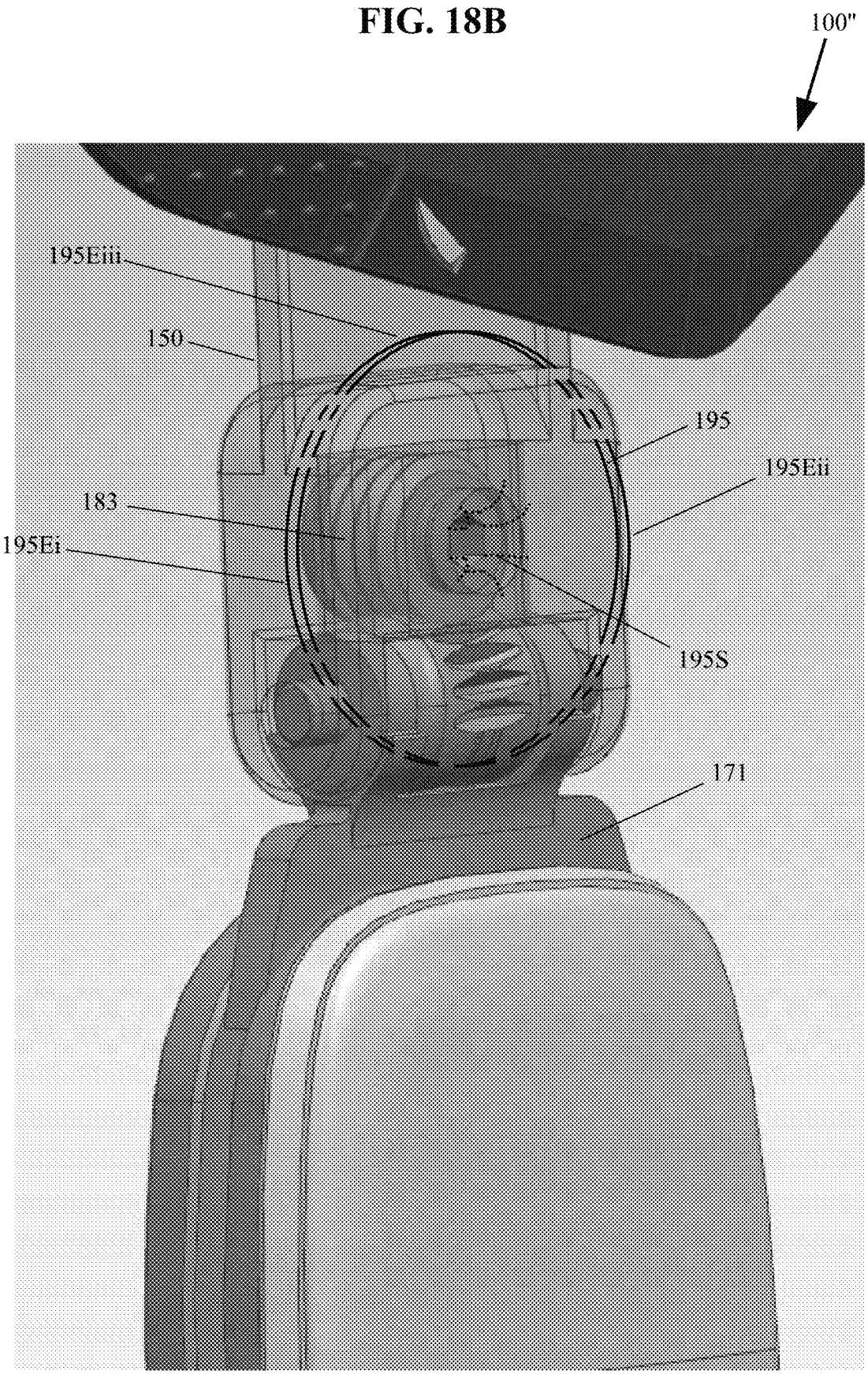
FIG. 18B is the transparent view of FIG. 18, but showing yet another version of the worm drive arrangement that includes an interior dial, portions of which protrude beyond the housing for use in making lateral rotational adjustments to the relative angle between the upper and lower cuffs.

As seen in FIG. 18A, the knee brace 100' may also have the separate worm gear/wheel 181 of the knee brace 200 instead be integrally formed with the hinge plate 171, and may have grooves 171G formed in that integral part. In addition, rather than having to use an Allen wrench tool to rotate the worm screw 183 for lateral rotational adjustments to the relative angle between the upper and lower cuffs about axis 180X, the knee brace 100' may include a knob 190. The knob 190 may have a shaft 190S that may be received in and secured to the recess 184R. The knob 190 may have undulations or knurling or radial protrusions 191 that may be finger graspable to be easier to rotate the knob and thus the worm gear/wheel 181. For a knee brace 100" shown in FIG. 18B, rather than utilizing the exterior knob, a dial 195 may be positioned within the gear housing. The dial 195 may have a shaft 195S received in and secured to the recess 184R, and only portions of the dial (e.g., the left side 195Ei, the right side 195Eii, and the uppermost side 195Eiii) may protrude and be exposed beyond openings in the housing, permitting a physician to rotate the exposed dial portions to make lateral rotational adjustments to the relative angle between the upper and lower cuffs.

Figure 34:
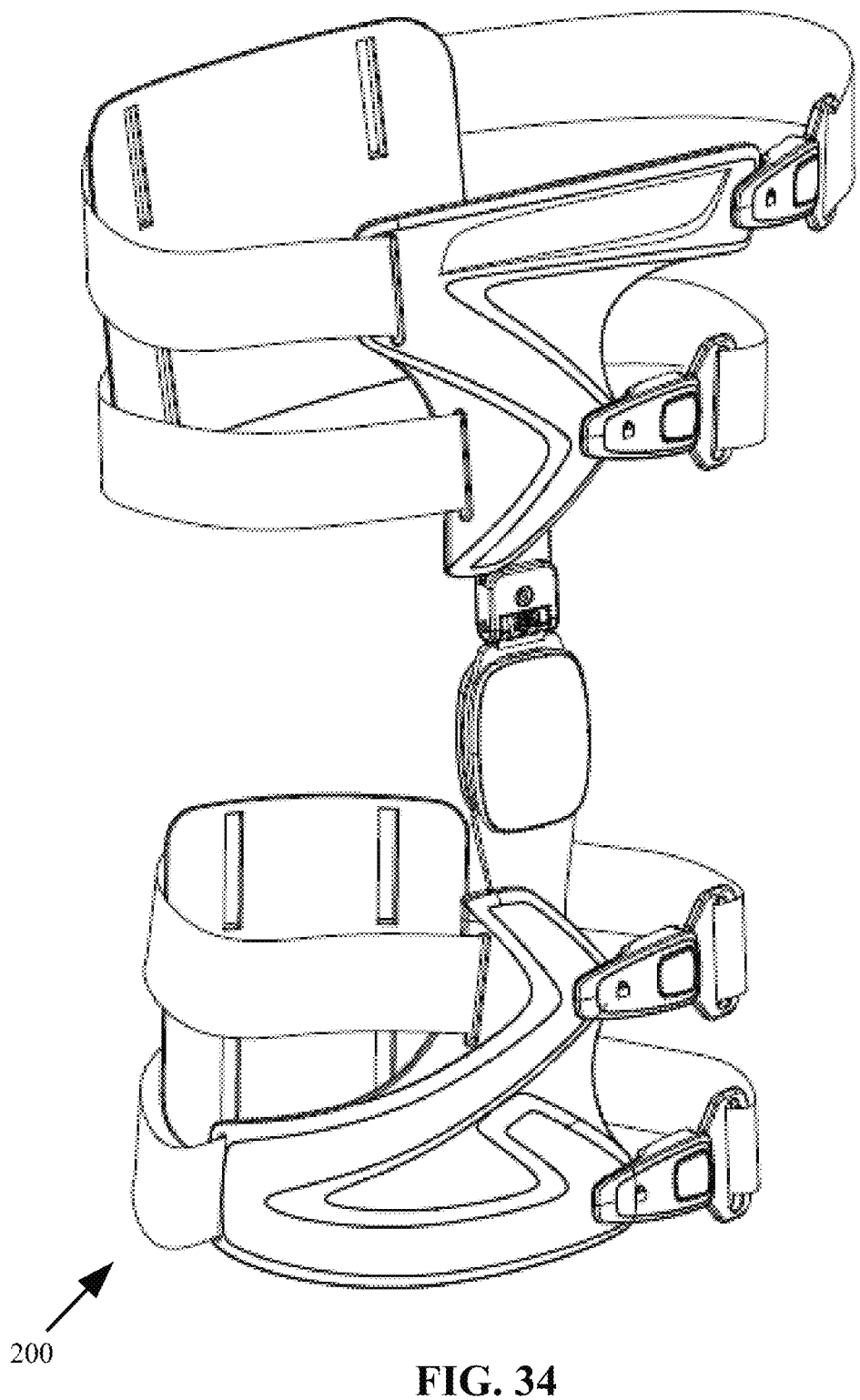
FIG. 34 is a first perspective view of a second embodiment of a knee brace as disclosed herein.
Figure 35:
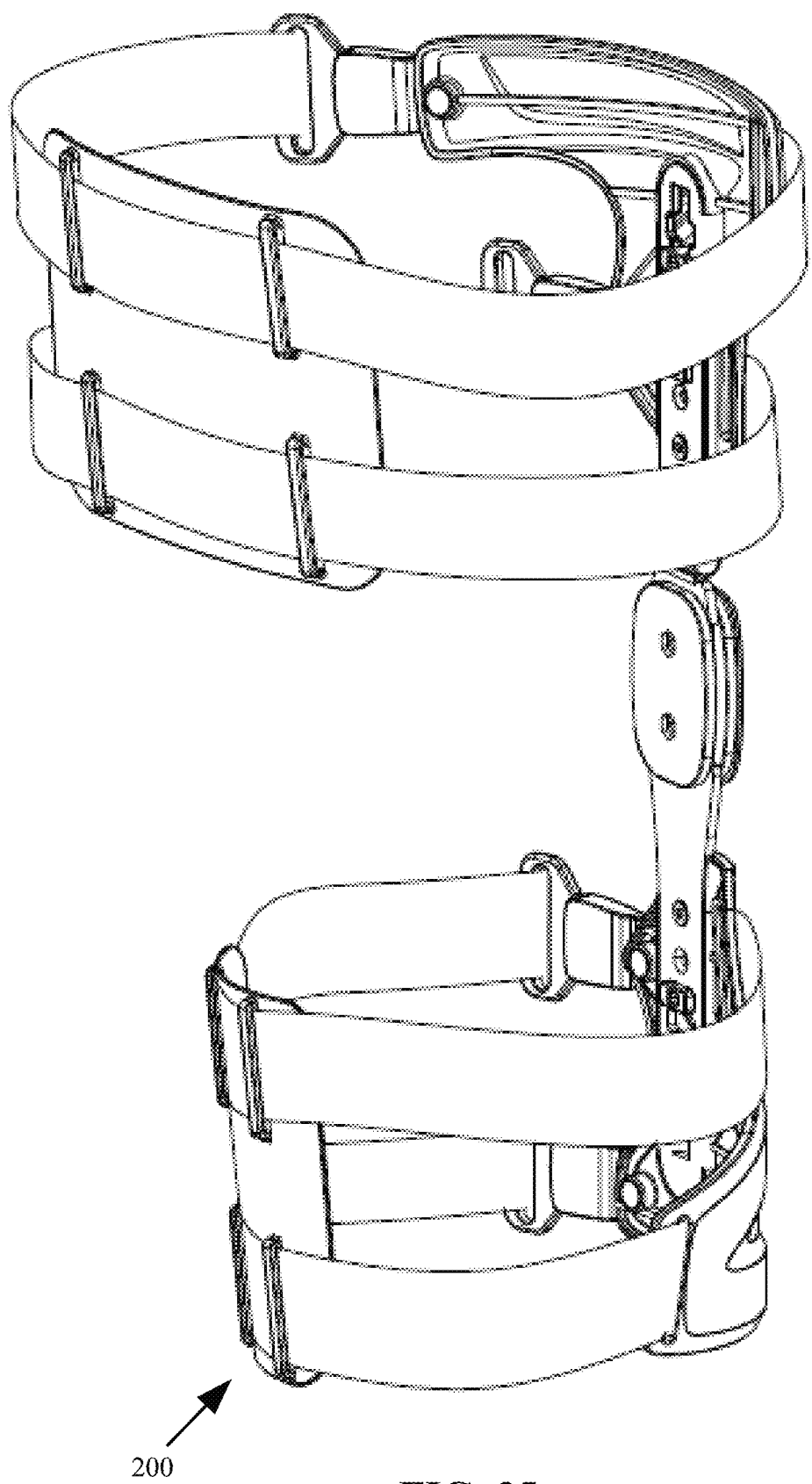
FIG. 35 is a second perspective view of the knee brace shown in FIG. 34.

As seen in FIGS. 34-36, in a second embodiment a knee brace 200 may be formed similar to knee brace 100, but may have a different peripheral shape for the upper shell and pad, and also for the lower shell and pad.

Figure 43:
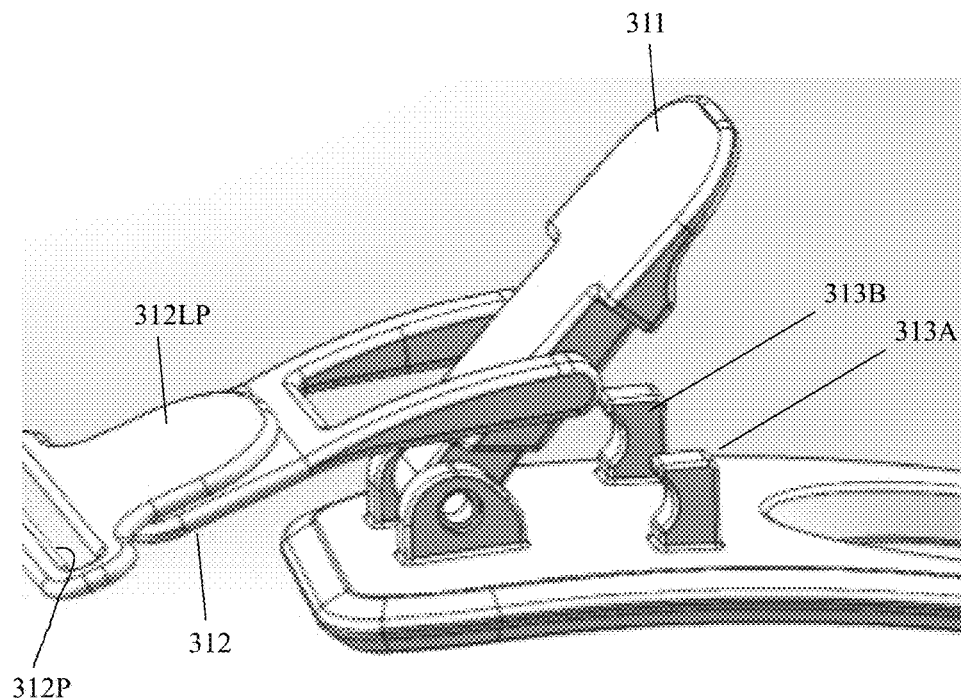
FIG. 43 illustrates a buckle that may be used to secure the brace to a wearer's leg, being shown in the unbuckled position.
Figure 44:
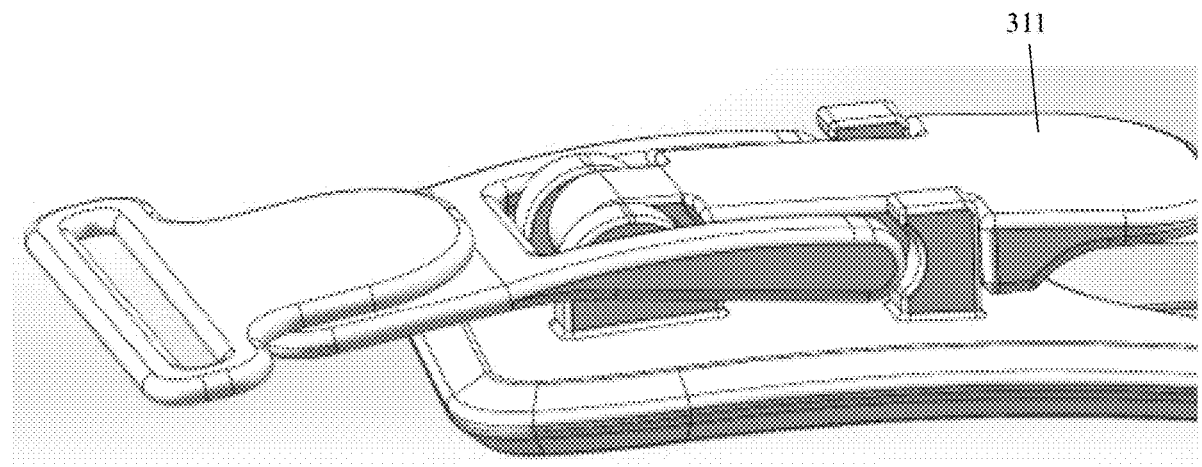
FIG. 44 is the buckle of FIG. 44, shown in the buckled position.
Figure 45:
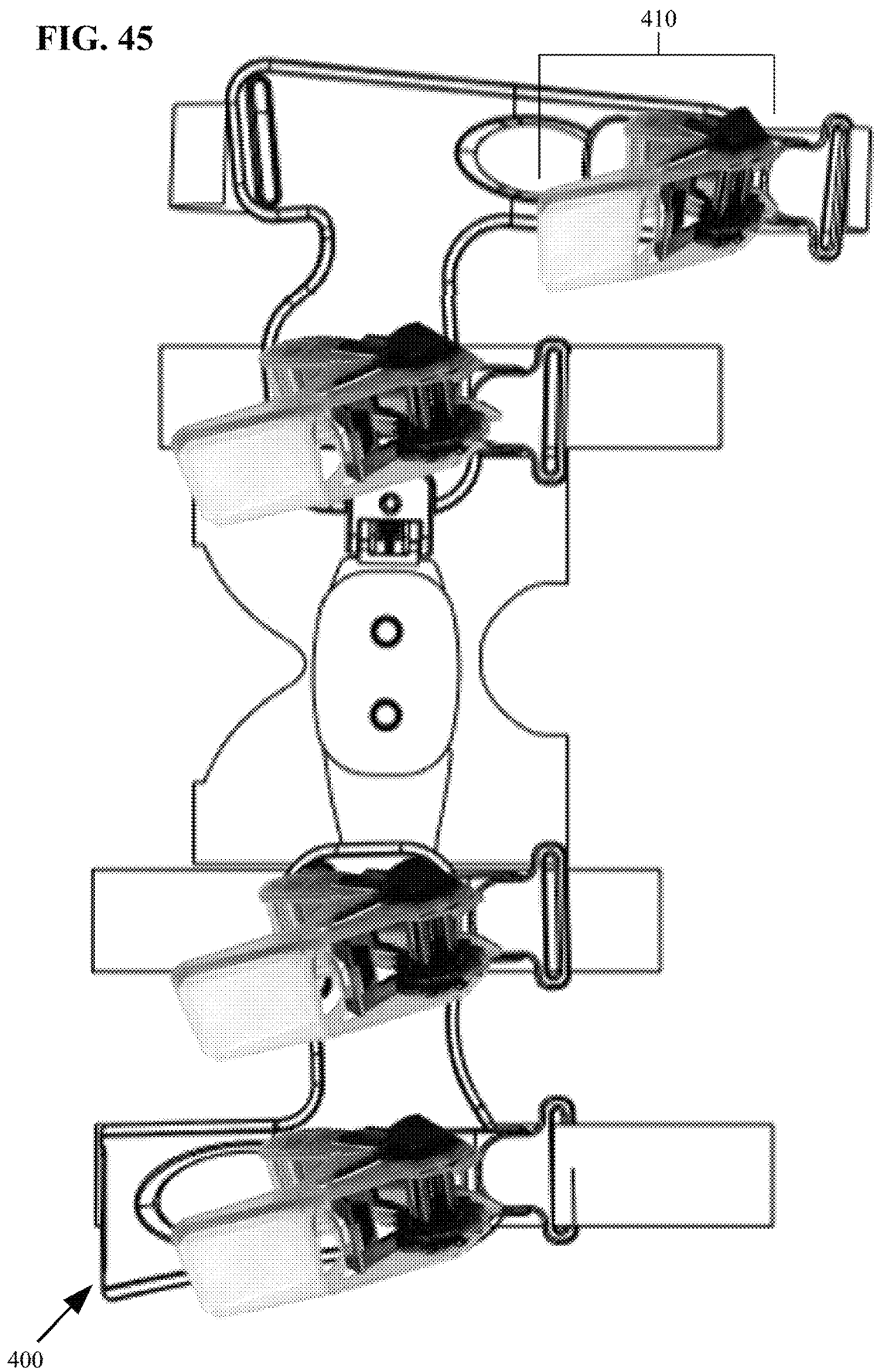
FIG. 45 is a front view of a fifth embodiment of a knee brace as disclosed herein, having a ratcheting buckle arrangement.
Figure 46:
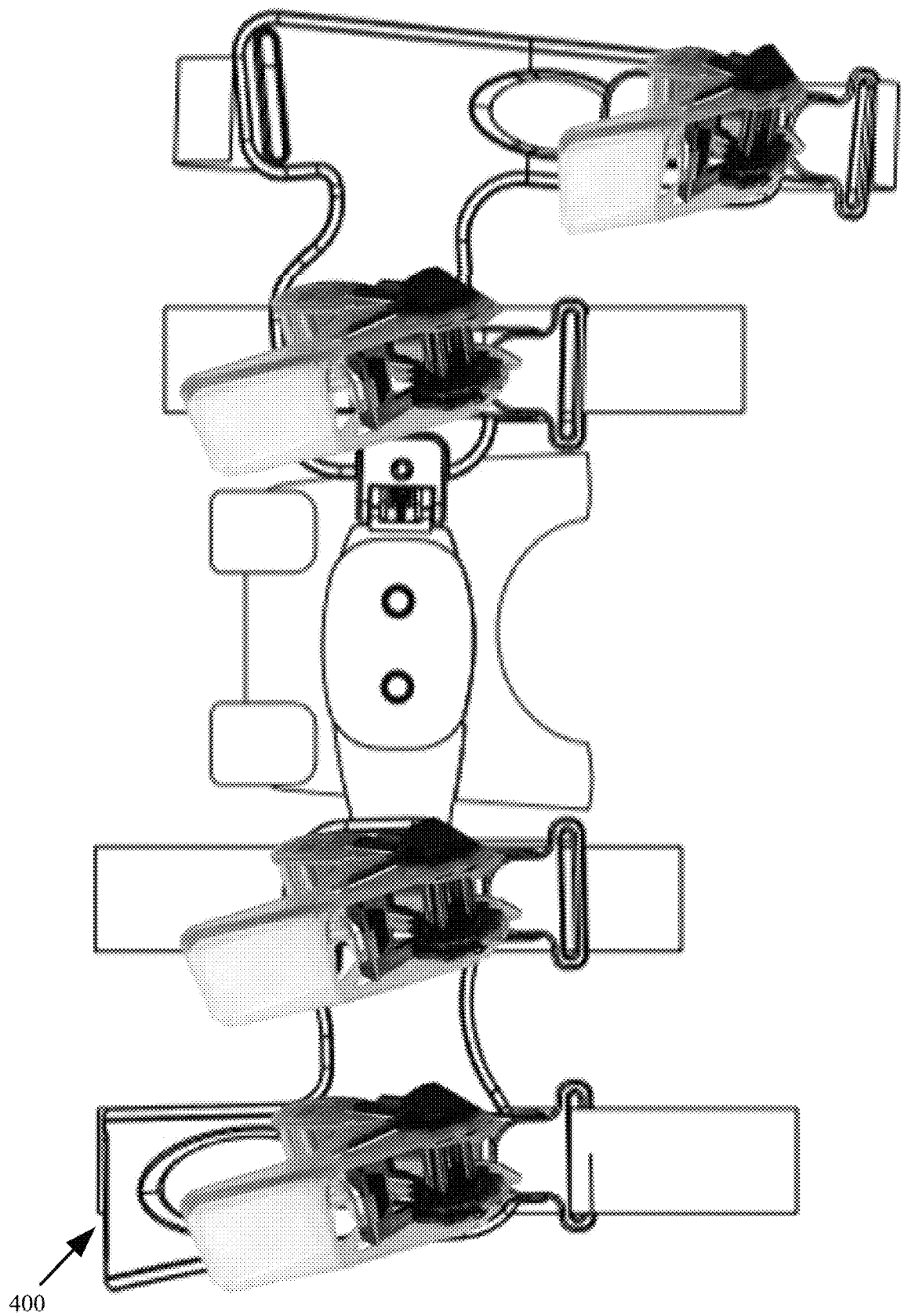
FIG. 46 is a different version of the knee brace of FIG. 45.
Figure 47:
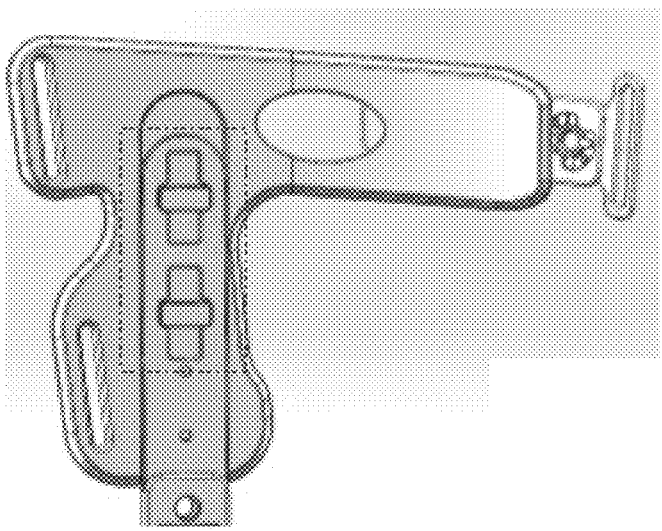
FIGS. 47-49 show coupling of the shell to an extension member, and movement to each of first and a second height adjustment positions.
Figure 48:
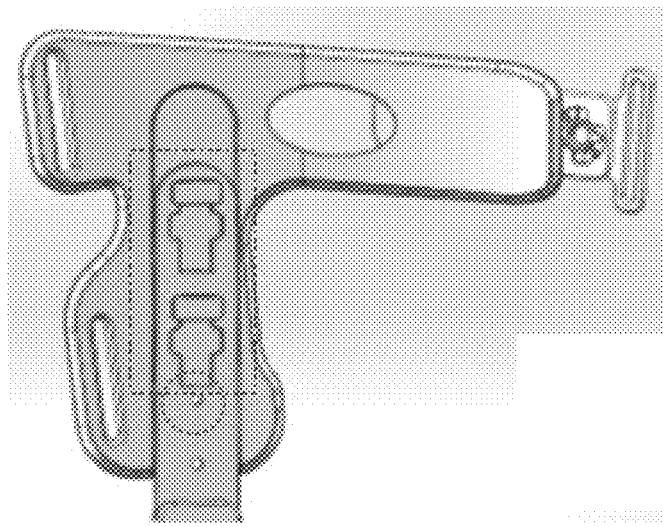
Figure 49:
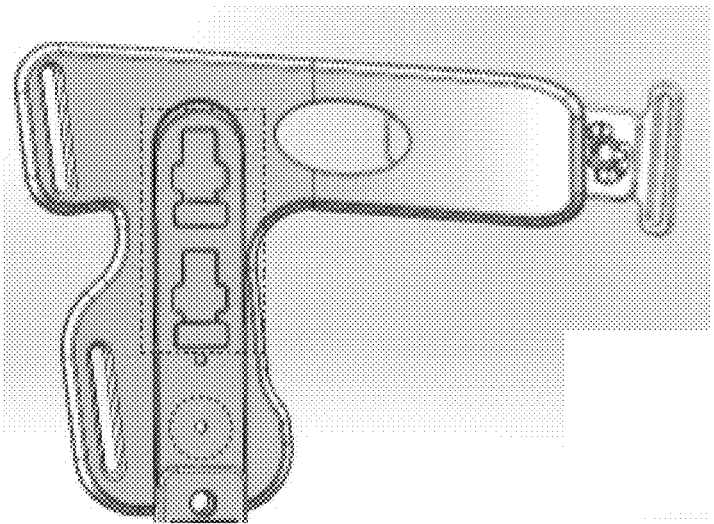

As seen in FIGS. 37-41, in a third embodiment a knee brace 300 (and 300' with a different knee sleeve portion) may each be formed similar to knee brace 200, but may also include a levered, snap in place, buckle arrangement 310 for each of the straps. As seen in FIGS. 43 and 44, the levered buckle arrangement 310 may include a lever arm 311, one end of which may be pivotally coupled to the shell. The strap may be coupled to an opening 312P formed at a first end of an attachment member 312, and the second end of the attachment member may terminate in a pair of arms that may each be pivotally coupled to the lever arm 311 between its first and second ends. Each of the ends of the pair of arms of the attachment member 312 may be rounded, and may be positioned to respectively engage a correspondingly rounded side surface on each of a pair of protrusions 313A and 313B that extend away from the upper shell, to releasably secure the lever arm in the closed position shown in FIG. 44. The distal end of the lever arm 311 may be configured to be lifted by the wearer's fingers to disengage the ends of the pair of arms of the attachment member 312 from the rounded side surface on each of a pair of protrusions 313A and 313B to unlock the buckle. The attachment member 312 may also be provided with a lift point 312LP for opening the locked strap, which feature has been curved and slightly elevated to work with the fingers more easily particularly for the case where a person using the brace may have arthritis or other hand functionality issues, so that the buckle can be released by the palm portion of the hand.

As seen in FIGS. 45-52, in a fourth embodiment a knee brace 400 may be formed similar to knee brace 300, but instead of the levered snap in place buckle arrangement it may utilize a ratcheting buckle arrangement 410 for tensioning of the strap. The ratcheting buckle arrangement 410 may be the same as, or similar to, the arrangements shown by the following U.S. Pat. No. 3,749,366 to Brucker; U.S.

Pat. No. 3,662,435 to Allsop; U.S. Pat. No. 4,185,360 to Prete; and U.S. Pat. No. 6,547,218 to Landy.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A knee brace comprising:
   an upper cuff comprising:
      a shell, said shell comprising: a plurality of ventilation openings; and
      a pad, said pad secured to said shell; said pad comprising:
         a plurality of through openings; at least a portion of each of said plurality of through openings in said pad being positioned to interconnect with a respective one of said plurality of ventilation openings in said shell; and
         a plurality of grooves; wherein each adjacent pair of said plurality of through openings in said pad are interconnected by one of said plurality of grooves;
   means for securing said upper cuff to a leg of a wearer above the knee;
   a lower cuff, said lower cuff comprising:
      a shell, said shell of said lower cuff comprising: a plurality of ventilation openings; and
      a pad, said pad of said lower cuff secured to said shell of said lower cuff; said pad of said lower cuff comprising:
         a plurality of through openings; at least a portion of each of said plurality of through openings in said pad of said lower cuff being positioned to interconnect with a respective one of said plurality of ventilation openings in said shell of said lower cuff; and
         a plurality of grooves; wherein each adjacent pair of said plurality of through openings in said pad of said lower cuff are interconnected by one of said plurality of grooves on said pad of said lower cuff;
   means for securing said lower cuff to the leg of the wearer below the knee; and
   means for pivotally coupling said upper cuff to said lower cuff.

2. The knee brace according to claim 1, wherein said plurality of openings and said grooves of each said pad are distributed over at least 80 percent of its surface area.

3. The knee brace according to claim 2,
   wherein said shell and said pad for said upper cuff are molded into a curved shape to correspond to a curvature of the wearer's leg above the knee; and
   wherein said shell and said pad for said lower cuff are molded into a curved shape to correspond a curvature of the wearer's leg below the knee.

4. The knee brace according to claim 2, wherein each said pad is made of a material from the group of materials consisting of: ethylene-vinyl acetate; and rubber.

5. A knee brace comprising:
   a lower cuff; said lower cuff configured for placement against a portion of the calf region of a wearer:
   an upper cuff; said upper cuff configured for placement against a portion of the thigh region of a wearer:
   an upper mounting stud, said upper mounting stud comprising: a first leg configured to protrude away from said upper cuff, and a second leg centrally positioned with respect to a distal end of said first leg to form a T-shape for said upper mounting stud;
   a hinge, said hinge comprising
      an upper arm, said upper arm comprising:
         a cruciform-shaped opening comprising:
            a central open portion, said central open portion configured to slidably receive said second leg of said T-shaped mounting stud therethrough in a first direction in a clearance fit;
            an upper open portion;
            a lower open portion; and
            wherein each of said upper open portion and said lower open portion are configured to slidably receive said first leg of said T-shaped mounting stud therethrough in respective second and third directions to alternatively couple said upper cuff to said upper arm at a first adjustment position or a second adjustment position;
      a lower arm; said lower arm being pivotally coupled said upper arm;
   means for securing said lower arm to said lower cuff;
   means for securing said lower cuff to the leg of the wearer below the knee; and
   means for securing said upper cuff to the leg of the wearer above the knee.

6. The knee brace according to claim 5, wherein said first arm and said second arm are shaped and pivotally coupled together to form a bicentric hinge.

7. The knee brace according to claim 6, further comprising:
   a first hole in said first arm;
   a second hole in said first arm;
   a threaded insert positioned in said upper cuff to align with said first hole in said first arm when said T-shaped mounting stud is in said first adjustment position, and to align with said second hole in said first arm when said T-shaped mounting stud is in said second adjustment position; and
   a fastener configured to be threadably received in said threaded insert to secure said first arm to said upper cuff.

8. The knee brace according to claim 7, further comprising:
   a second said T-shaped mounting stud positioned a first distance away from said first T-shaped mounting stud; and
   a second said cruciform-shaped opening in said upper arm positioned a second distance away from said first cruciform-shaped opening, said second distance being the same as said first distance.

9. A knee brace comprising:
   a lower cuff; said lower cuff configured for placement against a portion of the calf region of a wearer:
   means for securing said lower cuff to the leg of the wearer below the knee;
   an upper cuff; said upper cuff configured for placement against a portion of the thigh region of a wearer:
   means for securing said upper cuff to the leg of the wearer above the knee;

a hinge, said hinge comprising
  an upper plate:
  a lower arm; said lower arm secured to said lower cuff;
  wherein said upper plate and said lower arm are shaped and pivotally coupled together to form a bicentric hinge to respectively pivot about first and second parallel axes;
  wherein said upper plate comprises a worm gear, said worm gear comprising a plurality of gear teeth;
a worm screw, said worm screw comprising a helical screw thread;
an upper arm; said upper arm having a first portion secured to said upper cuff, and a second portion pivotally coupled to said upper plate; said upper arm configured to rotatably house said worm screw, with said helical screw thread of said worm screw positioned to sequentially engage said gear teeth of said worm gear, when said worm gear is rotated;
a dial secured to said worm gear and configured to rotate said worm gear to pivot said upper cuff about a third axis to a desired angle with respect to said lower cuff, said third axis being perpendicular to said first and second axes.

10. The knee brace according to claim 9, wherein said worm gear comprises at least nine gear teeth.

11. The knee brace according to claim 9, wherein said worm gear is integrally formed with said hinge plate.

12. A knee brace comprising:
  a lower cuff, said lower cuff configured for placement against a portion of the calf region of a wearer: said lower cuff comprising:
  a shell;
  a pad, said pad secured to said shell:
  a lower lever arm, a first end of said lower lever arm being pivotally coupled to said shell to pivot between a first position where a second end of said lower lever arm is proximate to said shell, and a second position where said second end of said lower lever arm is distal from said shell;
  a lower strap, a first end of said lower strap being fixedly secured to a first side of said shell; a second end of said lower strap being pivotally coupled to a portion of said lower lever arm between said first end of said lower lever arm and said second end of said lower lever arm;
an upper cuff; said upper cuff configured for placement against a portion of the thigh region of a wearer, said lower cuff comprising:
  a shell;
  a pad, said pad of said upper cuff secured to said shell of said upper cuff:
  an upper lever arm, a first end of said upper lever arm being pivotally coupled to said shell of said upper cuff to pivot between a first position where a second end of said upper lever arm is proximate to said shell of said upper cuff, and a second position where said second end of said upper lever arm is distal from said shell of said upper cuff;
  an upper strap, a first end of said upper strap being fixedly secured to a first side of said shell of said upper cuff; a second end of said upper strap being pivotally coupled to a portion of said upper lever arm being between said first end of said upper lever arm and said second end of said upper lever arm; and
means for pivotally coupling said upper cuff to said lower cuff.

13. The knee brace according to claim 12,
wherein said second end of said lower strap comprises a clevis member, said clevis member configured for said pivotal coupling to said lower lever arm; and
wherein said second end of said upper strap comprises a clevis member, said clevis member of said upper strap configured for said pivotal coupling to said upper lever arm.

14. The knee brace according to claim 12,
further comprising means for releasably securing said lower lever arm in said first position for cinching of said lower strap of said lower cuff about the leg of the wearer below the knee; and
further comprising means for releasably securing said upper lever arm in said first position for cinching of said upper strap of said upper cuff about the leg of the wearer above the knee.

\* \* \* \* \*